(12) United States Patent
Welker et al.

(10) Patent No.: US 10,766,970 B2
(45) Date of Patent: Sep. 8, 2020

(54) MODIFIED CARBOHYDRATES, COMPOSITIONS COMPRISING THE SAME, AND METHODS OF MAKING AND USING THE SAME

(71) Applicants: Wake Forest University Health Sciences, Winston-Salem, NC (US); Wake Forest University, Winston-Salem, NC (US)

(72) Inventors: Mark E. Welker, Clemmons, NC (US); Emmanuel C. Opara, Durham, NC (US); Surya R. Banks, Winston-Salem, NC (US); Amber N. Weissenfluh, Kernersville, NC (US)

(73) Assignees: Wake Forest University Health Sciences, Winston-Salem, NC (US); Wake Forest University, Winston-Salem, NC (US)

( * ) Notice: Subject to any disclaimer, the term of this patent is extended or adjusted under 35 U.S.C. 154(b) by 0 days.

(21) Appl. No.: 16/311,992

(22) PCT Filed: Jun. 30, 2017

(86) PCT No.: PCT/US2017/040283
§ 371 (c)(1),
(2) Date: Dec. 20, 2018

(87) PCT Pub. No.: WO2018/005964
PCT Pub. Date: Jan. 4, 2018

(65) Prior Publication Data
US 2019/0375860 A1 Dec. 12, 2019

Related U.S. Application Data

(63) Continuation-in-part of application No. 15/606,769, filed on May 26, 2017, now abandoned, and a continuation-in-part of application No. PCT/US2017/034748, filed on May 26, 2017.

(60) Provisional application No. 62/519,600, filed on Jun. 14, 2017, provisional application No. 62/357,741, filed on Jul. 1, 2016.

(51) Int. Cl.
*C08B 37/00* (2006.01)
*A61K 31/734* (2006.01)
*A61K 47/69* (2017.01)

(52) U.S. Cl.
CPC ........ *C08B 37/0084* (2013.01); *A61K 31/734* (2013.01); *A61K 47/6903* (2017.08)

(58) Field of Classification Search
None
See application file for complete search history.

(56) References Cited

U.S. PATENT DOCUMENTS

| 4,107,435 A | 8/1978 | Ross |
| 9,278,077 B2 | 3/2016 | DeBrouse |
| 2013/0041044 A1 | 2/2013 | Kurisawa et al. |
| 2016/0030360 A1 | 2/2016 | Vegas et al. |

FOREIGN PATENT DOCUMENTS

| CN | 102964610 | | 3/2013 | |
| CN | 106589409 | * | 4/2017 | .............. C08J 3/075 |
| CN | 106860422 | | 6/2017 | |
| WO | WO9929705 | * | 6/1999 | .............. C07H 15/00 |

OTHER PUBLICATIONS

Hou et al., "Enzymatically crosslinked alginate hydrogels with improved adhesion properties" Polymer Chemistry vol. 6 pp. 2204-2213 (Year: 2015).*
Boontheekul et al., "Controlling alginate gel degradation utilizing partial oxidation and bimodal molecular weight distribution" vol. 26 pp. 2455-2465 (Year: 2005).*
Kristiansen et al., "Periodate oxidation of polysaccharides for modification of chemical and physical properties" Carbohydrate Research vol. 345 pp. 1264-1271 (Year: 2010).*
Abulateefeh et al. "Synthesis and characterization of new derivatives of alginic acid and evaluation of their iron(iii)-crosslinked beads as potential controlled release matrices" Pharmaceutical Development and Technology, 19(7):856-867 (2014).
Dalheim et al. "Efficient functionalization of alginate biomaterials" Biomaterials, 80:146-156 (2016).
Follain et al. "Coupling of amines with polyglucuronic acid: Evidence for amide bond formation" Carbohydrate Polymers, 74:333-343 (2008).
Hou et al. "Enzymatically crosslinked alginate hydrogels with improved adhesion properties" Polymer Chemistry, 6:2204-2213 (2015).
International Search Report and the Written Opinion of the International Searching Authority corresponding to International Patent Application No. PCT/US17/34748 (9 pages) (dated Aug. 25, 2017).
International Search Report and the Written Opinion of the International Searching Authority corresponding to International Patent Application No. PCT/US17/40283 (11 pages) (dated Nov. 9, 2017).
Mei et al. "Novel Intestinal-Targeted Ca-Alginate-Based Carrier for pH-Responsive Protection and Release of Lactic Acid Bacteria" ACS Applied Materials & Interfaces, 6:5962-5970 (2014).
PubChem Compound Summary for CID 71544857, U.S. National Library of Medicine, https://pubchem.ncbi.nlm.nih.gov/compound/71544857 (10 pages) (2013).

(Continued)

*Primary Examiner* — Eric Olson
(74) *Attorney, Agent, or Firm* — Myers Bigel, P.A.

(57) ABSTRACT

Modified alginates are described herein along with hydrogels comprising the same. A modified alginate may be prepared by reacting alginate and an aromatic compound (e.g., an aromatic amine) and/or pH sensitive compound. The modified alginates, hydrogels, and/or methods described herein may be used to coat and/or encapsulate at least a portion of a bioactive substance, optionally for oral delivery in humans and other animals.

20 Claims, 3 Drawing Sheets

(56) References Cited

OTHER PUBLICATIONS

Tendulkar et al. "A three-dimensional microfluidic approach to scaling up microencapsulation of cells" Biomedical Microdevices, 14:461-469 (2012).
Yang et al. "Research progress on chemical modification of alginate: A review" Carbohydrate Polymers, 84:33-39 (2011).
Banks et al. "Chemical Modification of Alginate for Controlled Oral Drug Delivery" Journal of Agricultural and Food Chemistry (39 pages) (2019).
Partial supplementary European search report (Communication pursuant to Rule 164(1) EPC) corresponding to European Patent Application No. 17821354.2 (11 pages) (dated Feb. 17, 2020).

* cited by examiner

MODIFIED CARBOHYDRATES, COMPOSITIONS COMPRISING THE SAME, AND METHODS OF MAKING AND USING THE SAME

RELATED APPLICATION INFORMATION

This application claims the benefit of and priority to U.S. Provisional Patent Application Ser. Nos. 62/357,741 filed Jul. 1, 2016, and 62/519,600 filed Jun. 14, 2017; to U.S. application Ser. No. 15/606,769 filed May 26, 2017; and to PCT/US17/34748 filed May 26, 2017, the disclosure of each of which is incorporated herein by reference in their entirety.

FIELD

The present invention relates to modified carbohydrates (e.g., modified alginate) and compositions comprising a modified carbohydrate such as hydrogels comprising a modified carbohydrate. Also provided are methods of preparing and using a modified carbohydrate.

BACKGROUND

Certain therapeutic and bioactive substances, including, but not limited to, (i) medicines, drugs, enzymes, proteins, hormones, and vaccines, (ii) vitamins, minerals, micronutrients and other dietary supplements, (iii) probiotics and other micro-organisms, (iv) cells, cell parts, and/or biological materials, and (v) many other bioactive substances have been found to be vital, therapeutic and necessary for, among other things, the treatment, prevention, and/or inhibition of certain diseases and/or other conditions in humans and animals, the elimination or reduction of pain associated with a wide variety illnesses, diseases and conditions, and/or the general maintenance of good health and well-being in humans and animals, including pets and livestock. For many of these substances, the simplest and most cost-effective method for delivering the medicine or other substance to humans and animals is by oral delivery in the form of a pill, capsule, liquid, paste, or other currently available oral delivery method.

Current oral delivery methods, however, suffer from a number of significant drawbacks and limitations, depending on the substance being delivered. Chief among these is the fact that many substances taken orally are attacked, degraded and/or destroyed in the stomach by stomach acids and/or enzymatic action. This problem would benefit greatly from a viable and cost-effective oral delivery solution.

Even if a substance is not completely destroyed in the stomach by stomach acids and enzymatic action, however, the overall bioavailability and/or therapeutic efficacy of a particular substance, including micro-organisms, can be impacted or greatly reduced by such stomach acids and enzymatic action, depending on the particular substance being orally ingested. Live and active probiotic cultures are one such example. Probiotics are living micro-organisms that naturally reside in the human intestine, and which scientific research has established are vital to a properly functioning immune system, and to our overall physical health and well-being. Through a variety of factors such as disease or the use of antibiotics, the normal balance of "good" versus "bad" bacteria in the intestine can be damaged or seriously impaired, and can even be fatal if left untreated. These imbalances in the microbiome of the intestine have been shown to have other important and vital effects on our health. Many of these imbalances can be, and have been, successfully addressed and treated through the use of live and active probiotic cultures.

In this regard, the US Food and Drug Administration (FDA) and World Health Organization in 2002 recommended that "the minimum viable numbers of each probiotic strain at the end of the shelf-life" be reported on labeling. However, most companies that give a number report the viable cell count at the date of manufacture, a number probably much higher than that which exists at the moment of consumption. Because of variability in storage conditions and amount of time that has elapsed before consuming probiotics, it is difficult to tell exactly how much live and active culture remains at the time of consumption. Due to these ambiguities, the European Commission placed a ban on putting the word "probiotic" on the packaging of such products because such labeling can be misleading.

As a result, most probiotics are either not alive when they are taken orally (and are therefore completely ineffective for recolonizing the gut with "good" or healthy bacteria), or if alive when taken, are often destroyed in the stomach by stomach acids and enzymatic action, leaving a relatively small amount, if any, of the probiotics that actually make it to the small intestine alive and intact, where they are then able to recolonize the gut with the "good" bacteria, or address certain flora deficiencies as needed. As a result of this problem, patients suffering from a *Clostridium difficile* infection (CDI), for example, must often resort to fecal microbiota transplants (FMT), in order to restore the colonic microflora by introducing healthy bacterial flora directly into the large intestine.

An easier and more cost-effective method of delivering sufficient numbers of live and active probiotic cultures into the small intestine by oral delivery would clearly be a substantial improvement over fecal transplants. In addition, oral delivery of sufficient numbers of live and active probiotics to treat lesser conditions and for the general maintenance of the gut microbiome, with its attendant health benefits, would constitute a significant improvement over current oral delivery methods, which can be inefficient and largely ineffective.

Another problem with many drugs, medicines and other bioactive and therapeutic substances currently administered orally is that oral ingestion of these substances can cause severe stomach upset, nausea, and/or vomiting. These adverse effects are well-known and well-documented, and often appear on the warning label for the medicine as potential side effects. Common aspirin, for example, many prescription pain medications, and many chemotherapy drugs and other medications can, and often do, cause severe stomach upset, nausea, and/or vomiting when taken orally. Millions of people around the world suffer daily from these negative and unpleasant side effects when taking various medications, and so a viable, cost-effective solution is needed and would be a welcome relief to millions of people.

As one example, popular and widely used prescription pain relief medications, many of which are comprised of opioid derivatives such as oxycodone, hydrocodone, codeine, morphine, fentanyl and others, cause stomach upset, nausea, and/or vomiting. These opioid-derived pain medications interact with opioid receptors in the brain and nervous system in order to relieve pain. There were about 300 million pain medication prescriptions written in 2016.

There are two major problems with prescription opioid-based and other pain medications. Number one, they cause stomach upset, nausea, and/or vomiting in a large number of people who take them as previously mentioned. Number two, they are routinely crushed into a powder by drug dealers, and sold to addicts and others who inhale, snort or smoke the powder, or liquify it and inject it directly into their veins or arteries. As a result of this fact, the U.S. is in the midst of a massive opioid epidemic that has been widely reported on and discussed in the media. It is estimated that in 2015 more than 33,000 people died from overdoses of prescription pain medications in the U.S. Annually, opioids kill more people than car accidents and guns, and are now the leading cause of accidental deaths in the U.S.

It would be highly desirable and beneficial to be able to (i) administer pain and other medications orally without encountering any of the negative side effects commonly associated with taking such medications orally (upset stomach, nausea, and vomiting), and (ii) increase the bioavailability and thereby the efficiency of the pain medication, thereby reducing the amount of the pain medication (or dose) required, and (iii) create an oral delivery method which prevents opioid-based pain medications from being concentrated or crushed into a powdered form for use by drug addicts and black market sellers, or makes it prohibitively difficult or expensive to do so.

In the case of the administering medicines and other bioactive and therapeutic substances orally to animals, including pets and livestock, there is the additional problem that many medicines and other bioactive substances do not taste good to the animal, and therefore the animal will refuse to take or eat the medicine or other substance, or will spit out all or a portion of the medicine or other bioactive substance, making it difficult to administer these therapeutic substances to animals. This also results in not knowing exactly how much medicine the animal has taken or ingested, and therefore creates uncertainty as to how effective the unknown dose taken will actually be. The oral administration of medicines and other bioactive substances to animals can also create unnecessary anxiety and trust issues between the animal and the person administering the medicine or other therapeutic substance, and bites and other injuries to persons administering such oral medications and other substances to animals have frequently occurred. This process can also result in the substantial additional expense of having to hire and use a veterinarian or other trained professional to successfully administer the medicine to the animal by injection or other means. Given the widespread nature of these problems, a viable and cost-effective solution would be beneficial and welcome.

Certain vitamins and other dietary supplements are essential to our health and well-being, and evidence-based clinical research supports their importance and wide-ranging health benefits. Among them are Vitamin D, Coenzyme Q10, and Omega-3 fatty acids (EPA/DHA). Omega-3 fatty acids are often sold in the form of fish or Krill oil, or are sold as supplements in a variety of forms. As a result of the established health benefits of these and other vitamins and dietary supplements, they are often recommended or prescribed by physicians. Evidence-based clinical research also strongly suggests these and other dietary supplements should be incorporated into many diets to ensure that sufficient amounts of these critical substances are available for our overall health and well-being.

With respect to omega-3 fatty acids, for example, research has shown that cultures that routinely eat foods with high levels of omega-3 fatty acids demonstrate a variety of health benefits, such as lower levels of depression. Omega-3 fatty acids may also aid in treating the depressive symptoms of bipolar disorder, and may be important for visual and neurological development in infants. When ingested in relatively high doses, it may lower inflammation, which may be important in treating asthma. Other research suggests omega-3 fatty acids may be useful in ameliorating and/or reducing symptoms associated with ADHD in some children, while at the same time enhancing their mental skills. Omega-3 fatty acids may also prove to be useful in the treatment or slowing the progression of Alzheimer's disease and dementia.

With respect to Vitamin D, research has shown it can be important in reducing inflammation (by acting on C-Reactive Protein). It is also thought to aid in reducing pain as well as the stress on joints. Vitamin D has also been implicated as a possible source of reducing rheumatoid arthritis, obesity, certain cancers, various heart diseases, and the effects of radiation, while enhancing individuals' mental capacity, the immune system, bone growth, and the proper production of insulin. Although vitamin D can be procured by exposure to sunlight and other ways, vitamin D can also be attained by oral administration in a supplement form.

With respect to Coenzyme $Q_{10}$, it is a substance that helps convert food into energy, is found in almost every cell in the body and it is a powerful antioxidant. It is also critical in fulfilling the energy requirements of different organs such as the liver, heart and kidney. It is soluble in oil and present in most eukaryotic cells such as mitochondria. $CoQ_{10}$ is involved in the electron transport chain and participates in aerobic cellular respiration which generates energy. Over ninety percent of the human body's energy is generated this way. $CoQ_{10}$ is widely used in numerous applications as an antioxidant. There is also increasing use of $CoQ_{10}$ in medical applications like heart disease, eye care, cancer treatment, obesity and Huntington's disease.

These and other oil-based dietary supplements, however, face the industry-wide problem of oxidation, which results in the formation of toxic peroxides and other undesirable substances. This oxidation results in degradation of the substance, spoliation, and often a foul and offensive smelling odor and bad breath, all of which can be a strong disincentive for purchasing or taking these supplements again. As a result, dietary supplements such as omega-3 fatty acids, $CoQ_{10}$ and vitamin D are hampered by oxidation in storage, as well as by the intrinsic properties of the digestive tract, especially the pH differential along the digestive tract. The variable pH from the stomach to the intestine impacts the stability of the substance, and thereby the bioavailability of fat and peptide-based dietary supplements and other bioactive substances. Thus, the bioavailability of these and other dietary supplements are hampered by oxidation in storage, and by the digestive process in the stomach when taken orally.

As a result of these and other problems associated with the oral administration of various bioactive substances, it would be highly desirable and beneficial to have a method of orally delivering these substances to humans and animals, which increases bioavailability and, at the same time, eliminates many of the problems associated with the current oral delivery of these bioactive substances, some of which were discussed above.

BRIEF SUMMARY

One aspect of the present invention is a modified carbohydrate, such as a modified alginate or a modified hyaluronic acid. In some embodiments, the modified carbohydrate (e.g., modified alginate) comprises a structure of Formula I and/or Formula II.

Another aspect of the present invention is a hydrogel comprising a modified carbohydrate (e.g., a modified alginate) of the present invention. In some embodiments, the hydrogel may be a chemically modified alginate hydrogel. The hydrogel may comprise a modified carbohydrate that has been prepared by combining an aromatic compound with a carbohydrate (e.g., alginate). In some embodiments, the aromatic compound has one or more amines. The chemical structure of alginate may be modified using different amines and/or different methods, including: (i) covalently bonding aminoethyl benzoic acid to the carbohydrate (e.g., alginate)backbone, and/or (ii) oxidizing the vicinal diol in the carbohydrate (e.g., alginate) chain to an aldehyde before coupling to aminoethyl benzoic acid. In some embodiments, the aromatic compound is dopamine.

A chemically modified carbohydrate (e.g., modified alginate) and methods used may be utilized to coat and/or encapsulate at least a portion of one or more bioactive substances, such as, e.g., bioactive substances for oral delivery in humans and/or animals, including, but not limited to: (i) medicines, drugs, enzymes, proteins, hormones, and vaccines, (ii) vitamins, minerals, micronutrients and other dietary supplements, (iii) probiotics and other micro-organisms, (iv) cells, cell parts, and/or other biological materials, and/or (v) many other bioactive substances.

In some embodiments, a hydrogel of the present invention comprises an iodide, such as, but not limited to, potassium iodide, optionally wherein at least a portion of the iodide is coated and/or encapsulated by the hydrogel.

As used herein, the term "bioactive substance" means a substance used by and/or having any biological effect on a living organism, and includes, but is not limited to, prescription and non-prescription medications and drugs, chemicals, chemical compounds, molecules, enzymes, proteins, hormones, vaccines, vitamins, minerals, micronutrients and other dietary supplements, probiotics and other micro-organisms, cells, cell parts (including DNA and RNA), and other biological materials, as well as other bioactive compounds and substances.

Current oral delivery methods suffer from a number of significant drawbacks and limitations, depending on the substance being delivered. Chief among these is the fact that many substances taken orally are attacked, degraded and/or destroyed in the stomach by stomach acids and/or enzymatic action. Even if a substance is not completely destroyed in the stomach by stomach acids and enzymatic action, the overall bioavailability and/or therapeutic efficacy of a particular bioactive substance can be impacted or greatly reduced by such stomach acids and enzymatic action. Another problem with many drugs, medicines and other therapeutic substances taken orally is that oral ingestion of these substances can cause severe stomach upset, nausea, and/or vomiting.

Another aspect of the present invention relates to a method of protecting a bioactive substance (e.g., a medicine) from attack by an acid and/or an enzyme (e.g., enzymatic action in the stomach) by coating and/or encapsulating at least a portion of the bioactive substance in a modified carbohydrate (e.g., modified alginate) hydrogel of the present invention. In some embodiments, upon administration of a hydrogel of the present invention to a subject, when the hydrogel comprising the bioactive substance reaches the small intestine, it may be released into the small intestine by diffusion due to the pH differential, and/or as the hydrogel falls apart, and may thereby increase the overall bioavailability and/or effectiveness of the bioactive substance. This method of encapsulation and oral delivery may eliminate certain problems and/or adverse side effects often associated with the oral delivery of various medicines and other bioactive substances in humans and/or animals. Accordingly, this modified carbohydrate hydrogel, its methods of preparation, and its uses, whereby medicines and other bioactive substances are encapsulated for oral delivery to humans and/or animals, may provide a wide variety of health benefits, while potentially eliminating certain problems and/or adverse side effects often associated with the oral delivery of these medicines and other bioactive substances.

A further aspect of the present invention includes various compositions and/or combinations that are micro-encapsulated in a modified carbohydrate (e.g., modified alginate) and/or produced in a size suitable for injection, either by itself, or in combination with liposomes, micelles, and/or nanospheres for, among other things, targeted delivery to a specific site or group of cells in humans and/or animals, such as to a tumor site.

In some embodiments, a compound of the present is an aromatic compound (e.g., an aromatic compound comprising one or more amines) that is combined with a carbohydrate (e.g., alginate). In some embodiments, dopamine is combined with alginate. In some embodiments, for example, a modified alginate comprises 4-(2-ethylamino)benzoic acid alginate. In some embodiment, a modified alginate comprises dopamine modified alginate.

In some embodiments, a modified alginate comprises an aromatic substituent. The aromatic substituent may be an amine substituent, including, but not limited to, a 4-(2-ethylamino)benzoic acid derivative, a 4-(2-ethylamino)phenolic derivative, a 4-(2-ethylamino)anilinic derivative, or a para (2-ethylamino)toluenic (i.e., (2-ethylamino)4-methylbenzene) derivative, and/or mixtures thereof.

In some embodiments, the aromatic substituent is a dopamine substituent, including, but not limited to, a 4-(2-ethylamino)phenolic substituent, a 4-(2-ethylamino)benzoic acid substituent, a 4-(2-ethylamino)anilinic substituent, a 4-(2-ethylamino)toluenic substituent, and/or mixtures thereof.

In some embodiments, the present invention relates to alginate compounds and methods of preparing said alginate compounds for encapsulating a bioactive substance. In some embodiments, a modified alginate of the present invention is a dopamine-modified alginate (DMA), optionally prepared using one and/or two different methods and/or preparations. A modified alginate of the present invention may be characterized and/or quantified by a $^1$H-NMR methodology as described herein, which may quantify the amount of reactant (e.g., an aromatic amine such as, e.g., dopamine) that is incorporated into the alginate backbone.

Compositions of the present invention may protect the carbohydrate (e.g., alginate)encapsulated compound (e.g., bioactive substance such as medicines) at pH levels that are found in the stomach (e.g., pH of about 1-3), and may make the carbohydrate (e.g., alginate)encapsulated compounds available at pH levels that are found in the intestines (e.g., more basic pH levels of about 7-9). The alkaline environment may allow the carbohydrate (e.g., alginate)compound to be broken down and thus may provide for release of the encapsulated compound. The carbohydrate (e.g., alginate) encapsulated compounds may be protected at acidic pH levels by the carbohydrate (e.g., alginate)coupled to an aromatic amine compound.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

BRIEF DESCRIPTION OF THE DRAWINGS

The following drawings are provided to illustrate various aspects of the present inventive concepts and are not intended to limit the scope of the present invention unless specified herein.

DETAILED DESCRIPTION OF EXAMPLE EMBODIMENTS

Figure 1:
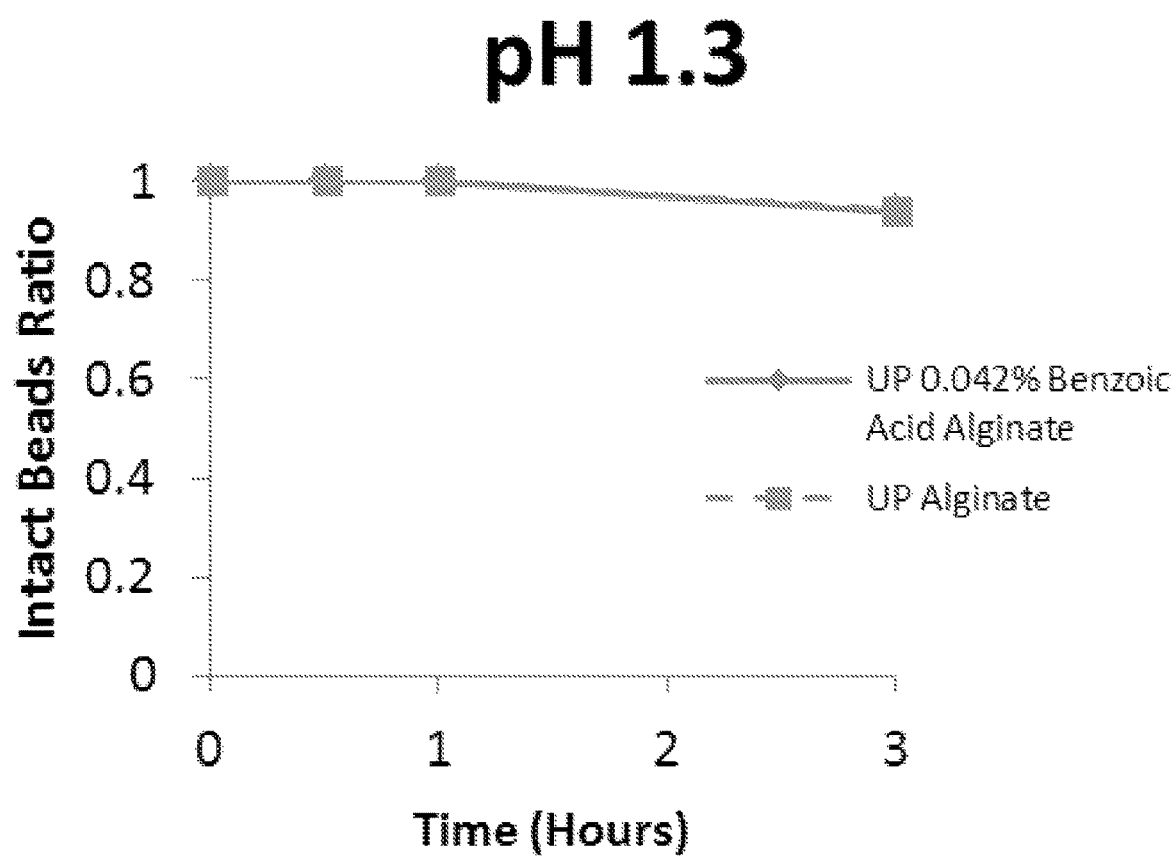
FIG. 1 shows a graph of the stability of unmodified and benzoic acid-modified alginate under acidic pH condition (pH 1.3).

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, 0.5%, or even ±0.1% of X. A range provided herein for a measurable value may include any other range and/or individual value therein.

Provided according to some embodiments of the present invention are modified carbohydrate compounds. In some embodiments, a modified carbohydrate of the present invention is a modified alginate or a modified hyaluronic acid. In some embodiments, a modified carbohydrate (e.g., a modified alginate) of the present invention comprises at least one structure unit having a structure of Formula I:

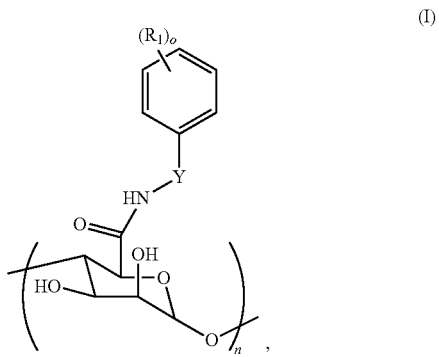

wherein
Y is absent or a $C_1$-$C_4$ alkyl or $C_1$-$C_4$ alkenyl;
$R_1$ is each independently selected from the group consisting of —H, —OH, —NH$_2$, —COOH, —NO$_2$, —CN, —Br, —Cl, —F, —$C_1$-$C_6$ alkylhalide, unsubstituted or substituted —$C_1$-$C_6$ alkyl, unsubstituted or substituted —$C_1$-$C_6$ alkenyl, —SO$_2$H, —SO$_3$H, —COCH$_3$, —Si(OH)$_3$, —SO$_2$NH$_2$, —PO(OR')$_2$, and —B(OH)$_2$, wherein each R' is independently selected from the group consisting of unsubstituted or substituted alkyl, alkenyl, alkynyl and aryl;
n is from 1 to 1,000,000; and
o is 0, 1, 2, 3, 4, or 5.

In some embodiments, the modified carbohydrate (e.g., a modified alginate) of Formula I has at least one $R_1$ that is selected from the group consisting of —OH, —NH$_2$, —COOH, —NO$_2$, —CN, —Br, —Cl, —F, —$C_1$-$C_6$ alkylhalide, unsubstituted or substituted —$C_1$-$C_6$ alkyl, unsubstituted or substituted —$C_1$-$C_6$ alkenyl, —SO$_2$H, —SO$_3$H, —COCH$_3$, —Si(OH)$_3$, —SO$_2$NH$_2$, —PO(OR')$_2$, and —B(OH)$_2$, wherein each R' is independently selected from the group consisting of unsubstituted or substituted alkyl, alkenyl, alkynyl and aryl. In some embodiments, the modified carbohydrate (e.g., a modified alginate) of Formula I has at least one $R_1$ that is hydrogen. In some embodiments, the modified carbohydrate (e.g., a modified alginate) of Formula I has at least one $R_1$ in the para position that is selected from the group consisting of —OH, —NH$_2$, —COOH, —NO$_2$, —CN, —Br, —Cl, —F, —C$_1$-C$_6$ alkylhalide, unsubstituted or substituted —C$_1$-C$_6$ alkyl, unsubstituted or substituted —C$_1$-C$_6$ alkenyl, —SO$_2$H, —SO$_3$H, —COCH$_3$, —Si(OH)$_3$, —SO$_2$NH$_2$, —PO(OR')$_2$, and —B(OH)$_2$. In some embodiments, at least one R$_1$ in a compound of Formula I may have a pKa in a range of about 3 to about 6 or about 4 to about 4.5. In some embodiments, at least one R$_1$ may have a pKa of about 3, 3.5, 4, 4.5, 5, 5.5, or 6.

In some embodiments, one or more functional groups in the modified carbohydrate (e.g., a modified alginate) of Formula I may be protonated or deprotonated, optionally one or more R$_1$ in the modified carbohydrate (e.g., a modified alginate) of Formula I may be protonated or deprotonated. In some embodiments, the protonation state (i.e., protonated or deprotonated) of one or more functional groups in the modified carbohydrate (e.g., a modified alginate) of Formula I may depend on the pH of the environment that the modified carbohydrate (e.g., a modified alginate) is exposed to and/or in contact with.

In some embodiments, a modified carbohydrate (e.g., a modified alginate) of the present invention comprises at least one structure unit having a structure of Formula II:

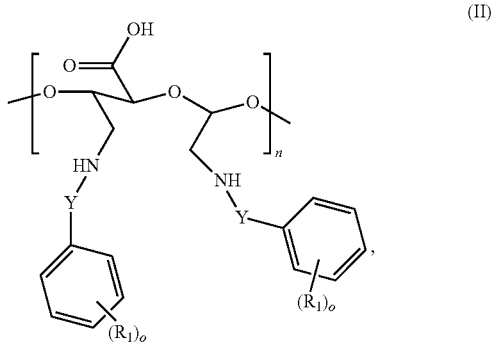

(II)

wherein
Y is absent or a C$_1$-C$_4$ alkyl or C$_1$-C$_4$ alkenyl;
R$_1$ is each independently selected from the group consisting of —H, —OH, —NH$_2$, —COOH, —NO$_2$, —CN, —Br, —Cl, —F, —C$_1$-C$_6$ alkylhalide, unsubstituted or substituted —C$_1$-C$_6$ alkyl, unsubstituted or substituted —C$_1$-C$_6$ alkenyl, —SO$_2$H, —SO$_3$H, —COCH$_3$, —Si(OH)$_3$, —SO$_2$NH$_2$, —PO(OR')$_2$, and —B(OH)$_2$, wherein each R' is independently selected from the group consisting of unsubstituted or substituted alkyl, alkenyl, alkynyl and aryl;
n is from 1 to 1,000,000; and
o is 0, 1, 2, 3, 4, or 5.

In some embodiments, the modified carbohydrate (e.g., a modified alginate) of Formula II has at least one R$_1$ that is selected from the group consisting of —OH, —NH$_2$, —COOH, —NO$_2$, —CN, —Br, —Cl, —F, —C$_1$-C$_6$ alkylhalide, unsubstituted or substituted —C$_1$-C$_6$ alkyl, unsubstituted or substituted —C$_1$-C$_6$ alkenyl, —SO$_2$H, —SO$_3$H, —COCH$_3$, —Si(OH)$_3$, —SO$_2$NH$_2$, —PO(OR')$_2$, and —B(OH)$_2$, wherein each R' is independently selected from the group consisting of unsubstituted or substituted alkyl, alkenyl, alkynyl and aryl. In some embodiments, the modified carbohydrate (e.g., a modified alginate) of Formula II has at least one R$_1$ that is hydrogen. In some embodiments, the modified carbohydrate (e.g., a modified alginate) of Formula II has at least one R$_1$ in the para position that is selected from the group consisting of —OH, —NH$_2$, —COOH, —NO$_2$, —CN, —Br, —Cl, —F, —C$_1$-C$_6$ alkylhalide, unsubstituted or substituted —C$_1$-C$_6$ alkyl, unsubstituted or substituted —C$_1$-C$_6$ alkenyl, —SO$_2$H, —SO$_3$H, —COCH$_3$, —Si(OH)$_3$, —SO$_2$NH$_2$, —PO(OR')$_2$, and —B(OH)$_2$. In some embodiments, at least one R$_1$ in a compound of Formula II may have a pKa in a range of about 3 to about 6 or about 4 to about 4.5. In some embodiments, at least one R$_1$ may have a pKa of about 3, 3.5, 4, 4.5, 5, 5.5, or 6.

In some embodiments, one or more functional groups in the modified carbohydrate (e.g., a modified alginate) of Formula II may be protonated or deprotonated, optionally one or more R$_1$ in the modified carbohydrate (e.g., a modified alginate) of Formula II may be protonated or deprotonated. In some embodiments, the protonation state (i.e., protonated or deprotonated) of one or more functional groups in the modified carbohydrate (e.g., a modified alginate) of Formula II may depend on the pH of the environment that the modified carbohydrate (e.g., a modified alginate) is exposed to and/or in contact with.

A modified carbohydrate (e.g., a modified alginate) of the present invention may be pH sensitive meaning that the protonation and/or ionic form of at least one functional group (e.g., R$_1$) in the modified carbohydrate (e.g., a modified alginate) may change over a pH range, such as, e.g., a pH range from about 1, 2, or 3 to about 7, 8, or 9. In some embodiments, a modified carbohydrate (e.g., a modified alginate) of the present invention may be pH sensitive and at least one R$_1$ may be a pH sensitive functional group such as, but not limited to, —OH, —NH$_2$, —COOH, —SO$_2$H, —SO$_3$H, —SO$_2$NH$_2$, —Si(OH)$_3$, or —B(OH)$_2$.

For simplicity, described herein are further embodiments with respect to certain carbohydrates, such as modified alginate, but it should be understood that other carbohydrates may be used.

A modified alginate of the present invention may be a chemically modified alginate. In some embodiments, a hydrogel of the present invention comprises a modified alginate of the present invention.

A modified alginate may be prepared by combining an aromatic compound with a carbohydrate, wherein the aromatic compound is one or more amines and the carbohydrate is an alginate. The chemical structure of alginate may be modified using different amines and/or different methods, such as, for example: (1) covalently bonding aminoethyl benzoic acid to the alginate backbone, and/or (2) oxidizing the vicinal diol in the alginate chain to an aldehyde before coupling to aminoethyl benzoic acid. In some embodiments, the aromatic compound is dopamine. The chemically modified alginate and/or methods of the present invention may be utilized to encapsulate a variety of bioactive substances for oral delivery in humans and/or animals, including, but not limited to: (i) drugs, medicines, enzymes, proteins, hormones, and vaccines, (ii) vitamins, minerals, micronutrients and/or other dietary supplements, (iii) probiotics and/or other microorganisms, (iv) cells, cell parts, and/or other biological materials, and/or (v) other bioactive substances.

Current oral delivery methods suffer from a number of significant drawbacks and limitations, depending on the substance being orally ingested. Chief among these is the fact that many substances taken orally are attacked, degraded and/or destroyed in the stomach by stomach acids and/or enzymatic action. Even if a substance is not completely destroyed in the stomach by stomach acids and/or enzymatic action, the overall bioavailability and/or therapeutic efficacy of a particular bioactive substance can be impacted or greatly reduced by such stomach acids and enzymatic action, depending on the substance being taken orally. Another problem with many drugs, medicines and other therapeutic substances administered orally is that oral ingestion of these substances can cause severe stomach upset, nausea, and/or vomiting.

According to some embodiments, provided herein are methods of protecting a bioactive substance (e.g., medicine) from attack by an acid and/or an enzyme (e.g., enzymatic action in the stomach) by encapsulating and/or coating at least a portion of the bioactive substance in a modified alginate hydrogel of the present invention. In some embodiments, when the encapsulated bioactive substance reaches the small intestine, it may be released into the small intestine by diffusion due to the pH differential, and/or as the hydrogel and/or microcapsule falls apart, which may thereby increase the overall bioavailability and effectiveness of the medicine or other bioactive substance. This method of encapsulation and oral delivery may eliminate certain problems and adverse side effects often associated with the oral delivery of various medicines and other bioactive substances in humans and animals. Accordingly, this novel modified alginate hydrogel, its methods of preparation, and its use to encapsulate medicines and other bioactive substances for oral delivery to humans and/or animals, may provide humans and/or animals with a wide variety of health benefits, while eliminating certain problems and/or adverse side effects often associated with the oral delivery of these medicines and other bioactive substances.

In some embodiments, various compositions and/or combinations may be coated and/or provided in micro-size suitable for injection, either by itself, or in combination with liposomes, micelles, and/or nanospheres, for targeted delivery to a specific site or group of cells in humans or animals, such as a tumor site.

In some embodiments, an aromatic compound comprising one or more amines may be combined with an alginate to prepare and/or provide a modified alginate of the present invention. In some embodiments, the aromatic compound is a dopamine. In some embodiments, the modified alginate is 4-(2-ethylamino)benzoic acid modified alginate. In some embodiments, the modified alginate is a dopamine modified alginate.

In some embodiments, a modified alginate of the present invention may comprise a 4-(2-ethylamino)benzoic acid derivative, a 4-(2-ethylamino)phenolic derivative, a 4-(2-ethylamino)anilinic derivative, and/or a para (2-ethylamino) toluenic (i.e., (2-ethylamino)4-methylbenzene) derivative. "Derivative" as used herein refers to a moiety that has been modified (e.g., chemically modified) to remove one or more functional groups (e.g., hydrogen, —OH, etc.), optionally to bind the derivative (e.g., covalently or non-covalently) to a parent moiety or compound (e.g., the aliginate backbone). In some embodiments, the methodology used to prepare a modified alginate of the present invention may use N-hydroxysuccinimide (NHS) optionally in conjunction with 1-ethyl-3-(3-dimethylaminopropyl)carbodiimide (EDC) to activate a carboxylic acid (or carboxylate) on an alginate, which may allow the primary amine on the aromatic substituent to react with the carboxylate to generate the amide.

In some embodiments, an alginate may be reacted with one or more reactants selected from the group consisting of 4-(2-aminoethyl)benzoic acid, 4-(2-aminomethyl)benzoic acid, 4-(2-aminoethyl)aniline, (2-ethylamino)4-methyl benzene, 4-(2-aminoacetyl)-benzoic acid, 4-(2-aminoethyl)salicylic acid, and/or 4-(2-aminomethyl)aniline and/or esters thereof. In some embodiments, the reactant is not dopamine. The alginate and reactant may be reacted in the presence of N-hydroxysuccinimide (NHS) and/or 1-ethyl-3-(3-dimethylaminopropyl)carbodiimide (EDC). In some embodiments, the alginate and reactant are reacted in the presence of a nitrile such as acetonitrile.

The reactant may be incorporated into alginate in an amount of about 1% to about 20% based on the average number of polysaccharide units in the alginate. In some embodiments, the reactant is incorporated into the alginate in an amount of about 1%, 2%, 3%, 4%, 5%, 6%, 7%, 8%, 9%, 10%, 11%, 12%, 13%, 14%, 15%, 16%, 17%, 18%, 19%, or 20%. In some embodiments, about 90%, 91%, 92%, 93%, 94%, 95%, 96%, 97%, 98%, 99%, or 100% of the reactant is chemically bond to the alginate, rather than free or trapped within the polymer.

Alginate used to prepare a modified alginate of the present invention may be of any type. Alginate is a polysaccharide composed of randomly oriented blocks of monomers of (1-4)-linked β-D-mannuronic acid (M) and α-L-guluronic acid (G). In some embodiments, a modified alginate of the present invention may be prepared and/or formed using an alginate having about 10%, 20%, 30%, 40%, 50%, 60%, 70%, 80%, or 90% of the total number of polysaccharide units be M units or G units. In some embodiments, the alginate used to prepare a modified alginate of the present invention may be a natural and/or unmodified alginate. In some embodiments, the alginate used to prepare a modified alginate of the present invention may be an oxidized alginate. In some embodiments, alginate may have a structure of Formula III:

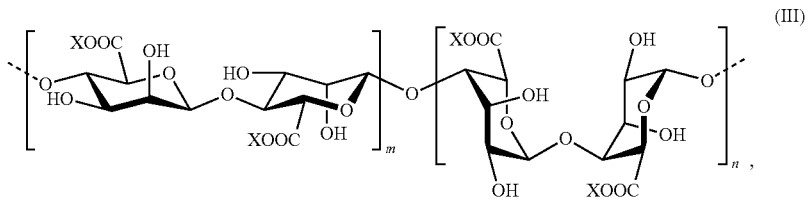

wherein:
X is hydrogen or a counterion (e.g., sodium, lithium, etc),
m is from 1 to 1,000,000, and
n is from 1 to 1,000,000.

In some embodiments, an alginate may be selected to prepare a modified alginate of the present invention in order to provide and/or tune the properties of a hydrogel comprising the modified alginate. For example, in some embodiments, the diffusion characteristics and/or diffusion rate may be adjusted and/or tuned for a hydrogel comprising a modified alginate of the present invention by the type of alginate used to prepare the modified alginate. In some embodiments, the rate of diffusion in a hydrogel comprising a modified alginate of the present invention may depend on the G fractions of alginate, with the diffusion coefficient increasing at lower G fractions. This may be attributed to the flexibility of the polymer backbone, suggesting that higher G fractions may result in higher crosslinking and/or less swelling, hence a greater barrier to diffusion. Measurements of simple physical parameters, such as volume fraction and size, may be used to predict solute transport in a hydrogel of the present invention. These parameters may be controlled based on the alginate concentration and/or composition for sustained release of small amounts of substances (e.g., bioactive substances) encapsulated in the modified alginate. In some embodiments, where the release of readily effective therapeutic levels is desired, it may be beneficial to modify alginate and/or a hydrogel of the present invention to release the encapsulated bioactive substance based on prompt degradation of the alginate and/or hydrogel. One way to achieve this immediate release and enhanced bioavailability of therapeutic molecules encapsulated in alginate hydrogel may be to modify the alginate polymer to degrade based on sensitivity to the basic pH of the small intestine where absorption into the systemic circulation also takes place. In some embodiments, a hydrogel of the present invention may degrade when exposed to a basic pH and thereby release at least a portion of the encapsulated substance (e.g., optionally in the small intestine of a subject). In some embodiments, the modification of an alginate with a reactant as described herein (e.g., an aromatic amine and/or pH sensitive compound) may shift the pKa of the alginate in solution and may provide sensitivity of the modified alginate and/or a hydrogel comprising the modified alginate to basic pH.

In some embodiments, alginate (e.g., a naturally occurring alginate and/or an oxidized alginate) may be covalently and/or noncovalently modified by adding a catechol and/or a pH sensitive functional group to the alginate backbone. In some embodiments, modifying alginate as described herein may improve the alginate's adhesive properties and/or its rigidity, which may improve performance of the modified alginate as a wound healing aid, surgical adhesive, and/or as a delivery vehicle.

In some embodiments, a carbohydrate and an aromatic compound (wherein both have reactive functionalities) may be reacted to generate a polymer that contains both a carbohydrate portion and an aromatic portion. For example, in an embodiment, the reaction may proceed as indicated below in Scheme I wherein X is a counterion that allows the carboxylate to make a salt, $R_1$ is each independently selected from substituents such as, but not limited to, —H, —OH, —NH$_2$, —COOH, —NO$_2$, —CN, —Br, —Cl, —F, —C$_1$-C$_6$ alkylhalide, unsubstituted or substituted —C$_1$-C$_6$ alkyl, unsubstituted or substituted —C$_1$-C$_6$ alkenyl, —SO$_2$H, —SO$_3$H, —COCH$_3$, —Si(OH)$_3$, —SO$_2$NH$_2$, —PO(OR')$_2$, and —B(OH)$_2$, wherein R' is unsubstituted or substituted alkyl, alkenyl, alkynyl, or aryl; m is 0 to 3 or 4; n is 1 to 1,000,000; and o is 1 to 3 or 5. In some embodiments, a modified alginate of the present invention may comprise two or more different $R_1$ or may comprise two or more of the same $R_1$. That is, for example, if o is 2, $R_1$ may be two hydroxyls, or alternatively, one of the $R_1$'s may be hydroxyl and the other $R_1$ may be a halide (or any other substituent identified herein).

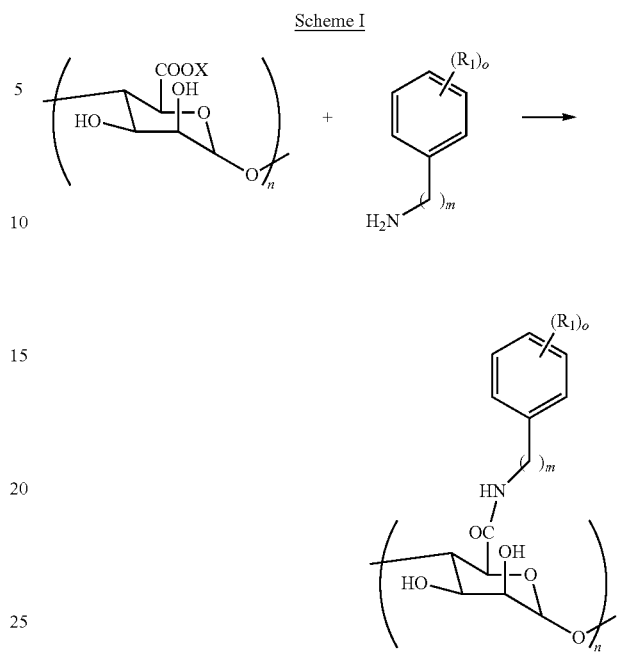

Scheme I

The reaction as shown in the diagram immediately above may be performed using alginates (as the carbohydrate). Alginic acid is a combination of β-D-mannuronic and α-L-guluronic acids attached with 1→4 linkages. Thus, although Scheme I is shown with only one type of carbohydrate, it should be understood that the respective sugars in the carbohydrate may be different. Similar to using alginic acid, it should be understood that other types of carbohydrates may be used such as, but not limited to, hyaluronic acid.

In some embodiments, a modified alginate may be prepared as illustrated in Scheme II, wherein X is hydrogen or a counterion; Y is absent or a C$_1$-C$_4$ alkyl or C$_1$-C$_4$ alkenyl; $R_1$ is each independently selected from the group consisting of —H, —OH, —NH$_2$, —COOH, —NO$_2$, —CN, —Br, —Cl, —F, —C$_1$-C$_6$ alkylhalide, unsubstituted or substituted —C$_1$-C$_6$ alkyl, unsubstituted or substituted —C$_1$-C$_6$ alkenyl, —SO$_2$H, —SO$_3$H, —COCH$_3$, —Si(OH)$_3$, —SO$_2$NH$_2$, —PO(OR')$_2$, and —B(OH)$_2$, wherein R' is unsubstituted or substituted alkyl, alkenyl, alkynyl, or aryl and o is 0, 1, 2, 3, 4, or 5. A modified alginate having a structure of Formula I may be provided.

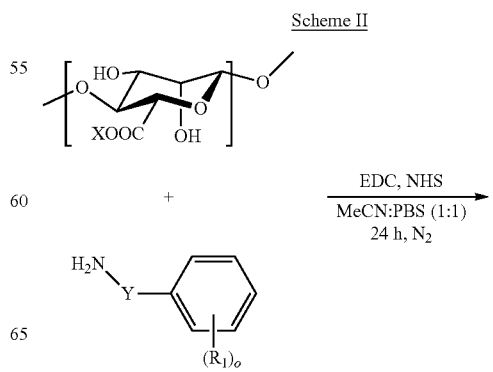

Scheme II

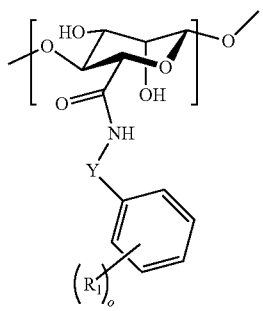

In some embodiments, a modified alginate may be prepared as illustrated in Scheme III, wherein X is hydrogen or a counterion; Y is absent or a $C_1$-$C_4$ alkyl or $C_1$-$C_4$ alkenyl; $R_1$ is each independently selected from the group consisting of —H, —OH, —NH$_2$, —COOH, —NO$_2$, —CN, —Br, —Cl, —F, —$C_1$-$C_6$ alkylhalide, unsubstituted or substituted —$C_1$-$C_6$ alkyl, unsubstituted or substituted —$C_1$-$C_6$ alkenyl, —SO$_2$H, —SO$_3$H, —COCH$_3$, —Si(OH)$_3$, —SO$_2$NH$_2$, —PO(OR')$_2$, and —B(OH)$_2$, wherein R' is unsubstituted or substituted alkyl, alkenyl, alkynyl, or aryl; and o is 0, 1, 2, 3, 4, or 5.

Scheme III

In some embodiments, a modified alginate may be prepared as illustrated in Scheme IV, wherein X is hydrogen or a counterion; Y is absent or a $C_1$-$C_4$ alkyl or $C_1$-$C_4$ alkenyl; $R_1$ is each independently selected from the group consisting of —H, —OH, —NH$_2$, —COOH, —NO$_2$, —CN, —Br, —Cl, —F, —$C_1$-$C_6$ alkylhalide, unsubstituted or substituted —$C_1$-$C_6$ alkyl, unsubstituted or substituted —$C_1$-$C_6$ alkenyl, —SO$_2$H, —SO$_3$H, —COCH$_3$, —Si(OH)$_3$, —SO$_2$NH$_2$, —PO(OR')$_2$, and —B(OH)$_2$, wherein R' is unsubstituted or substituted alkyl, alkenyl, alkynyl, or aryl; and o is 0, 1, 2, 3, 4, or 5. A modified alginate having a structure of Formula II may be provided.

Scheme IV

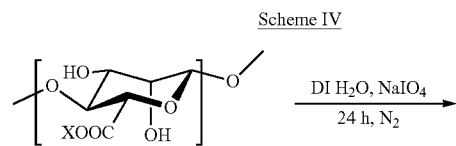

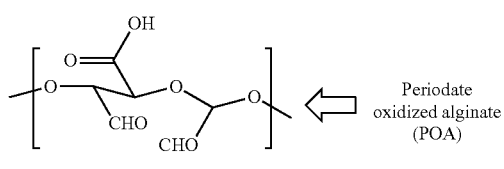

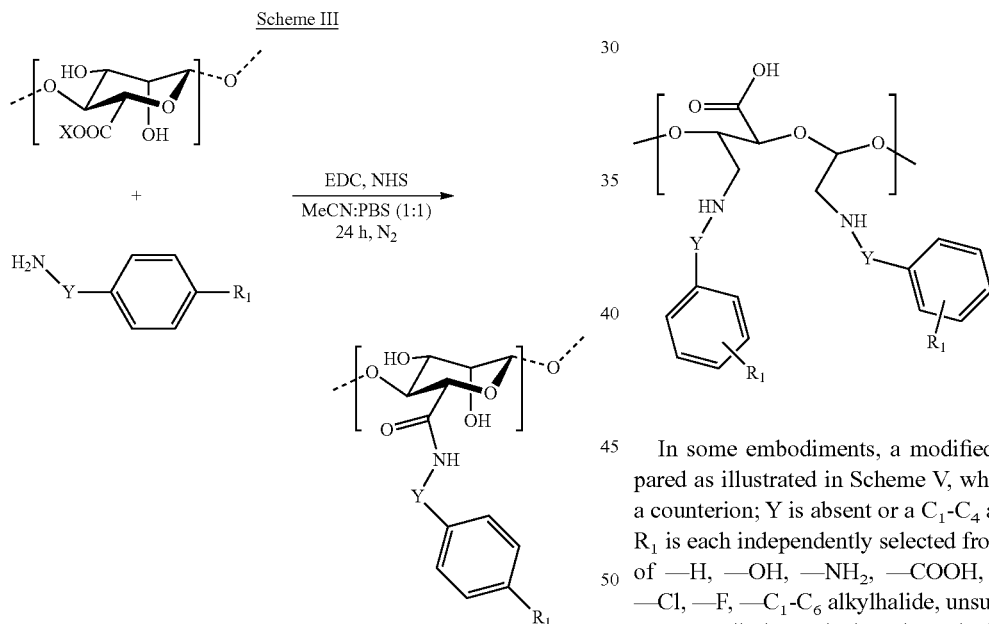

In some embodiments, a modified alginate may be prepared as illustrated in Scheme V, wherein X is hydrogen or a counterion; Y is absent or a $C_1$-$C_4$ alkyl or $C_1$-$C_4$ alkenyl; $R_1$ is each independently selected from the group consisting of —H, —OH, —NH$_2$, —COOH, —NO$_2$, —CN, —Br, —Cl, —F, —$C_1$-$C_6$ alkylhalide, unsubstituted or substituted —$C_1$-$C_6$ alkyl, unsubstituted or substituted —$C_1$-$C_6$ alkenyl, —SO$_2$H, —SO$_3$H, —COCH$_3$, —Si(OH)$_3$, —SO$_2$NH$_2$, —PO(OR')$_2$, and —B(OH)$_2$, wherein R' is unsubstituted or substituted alkyl, alkenyl, alkynyl, or aryl; and o is 0, 1, 2, 3, 4, or 5.

Scheme V

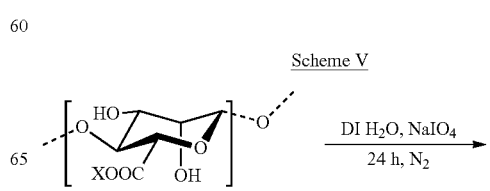

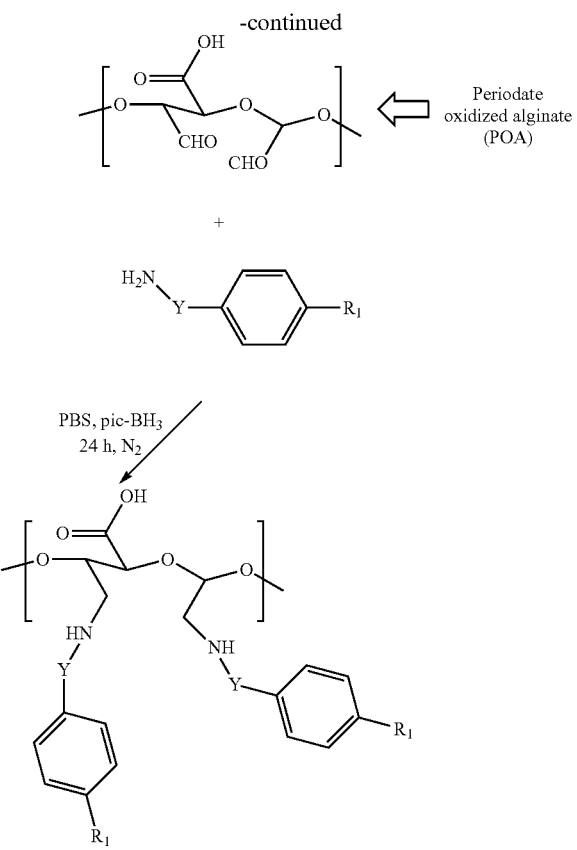

In some embodiments, alginic acid is combined with an aromatic as described in Schemes I-V, wherein X is sodium, m is 2, n is between about 500,000 and 1,000,000, o is 2, and the two $R_1$ are both hydroxyls. In some embodiments, the hydroxyls are positioned meta and para to the ethylamine (that is present on the phenyl group). In some embodiments, the carbohydrate is alginic acid, X is sodium, m is 2, n is between about 500,000 and 1,000,000, o is 1, and $R_1$ is amino or a carboxylate salt (or carboxylic acid).

In some embodiments, the aromatic substituent that reacts with alginic acid (or another carbohydrate) may be 4-aminomethyl benzene sulfonamide. Similar to the reaction shown in Scheme I, when 4-aminomethyl benzene sulfonamide is used for the aromatic substituent, n may be between about 500,000 and 1,000,000. In some embodiments, 4-aminomethyl benzene sulfonamide may contain additional substituents (e.g., 1, 2, or more) off the benzene ring, and the substituents may be amino, a carboxylate salt, and/or a carboxylic acid.

The reaction between the carbohydrate and an aromatic compound may be performed in a buffer such as, but not limited to, PBS (Phosphate Buffered Saline) and other buffers so long as they don't adversely affect the reaction. Additionally or alternatively, the reaction may take place in a nitrile such as, but not limited to, acetonitrile.

Although the reactions above in Scheme I-V are shown with varying linker group sizes (e.g., m can be 0 to 3 or 4; Y is absent or a C1-C4 alkyl or alkenyl group), and different functional groups on the aromatic ring, in some embodiments, maximal microencapsulation and/or coating may occur when the linker group is an ethylene. In some embodiments, one or more (e.g., 1, 2, 3, or more) protective groups may be utilized to get the desired reaction to proceed and/or to avoid having a plurality of different reaction processes occurring. These protective groups and their chemistry can be found in, for example, Greene's Protective Groups in Organic Synthesis, Fourth Edition, 2007, John Wiley & Sons, Inc., which is hereby incorporated by reference in its entirety.

In some embodiments, the present invention relates to alginate compounds and methods of preparing said alginate compounds, optionally for encapsulating and/or coating at least a portion of a bioactive substance such as, e.g., a bioactive substance to be delivered orally or by other means. In some embodiments, the modified alginate is an amine-modified alginate. In some embodiments, the modified alginate is a dopamine-modified alginate (DMA). A modified alginate may be characterized and/or quantified by a $^1$H-NMR methodology, such as, e.g., to quantify incorporation of a reactant (e.g., dopamine) into the alginate backbone.

Dopamine (i.e., (4-(2-aminoethyl) benzene, 1,2-diol)), for example, has three substituents, including an ethylene linker with a reactive amino group, such that it can be linked to alginate (or alginic acid). Without being bound by theory, the linker group may be of a sufficient length to allow microencapsulation of a bioactive substance such as, e.g., medicine, drug, protein, hormone, vaccine, vitamin, mineral, micronutrient and/or other dietary supplement, biological material, probiotic and/or other micro-organism, and/or another bioactive compound and/or substance. A modified alginate of the present invention may comprise a polar group (e.g., the carbohydrate portion) and a hydrophobic portion (e.g., an aromatic benzene ring), which may allow for microencapsulation. A modified alginate of the present invention, optionally when provided in a hydrogel of the present invention, may be used for protecting a bioactive substance from attack and/or degradation by an acid/or and an enzyme (e.g., enzymatic action in the stomach), which may enhance the bioavailability and/or effectiveness of the bioactive substance, optionally in the place where they are most useful and/or beneficial (e.g., in the intestines).

A modified alginate of the present invention may coat and/or encapsulate at least a portion of a compound (e.g., bioactive substance), and/or may protect the compound at pH levels that are found in the stomach (e.g., pH of about 1-3), but the modified alginate may allow and/or provide for the compound to be made available at the pH levels that are found in the intestines (e.g., more basic pH levels such as about 7-9) as the alkaline environment may allow for the alginate to be broken down, which may allow for access to and/or release of the encapsulated compound. The alginate encapsulated compounds may be protected at acidic pH levels by the modified alginate.

In some embodiments, the lability of a modified alginate and/or hydrogel of the present invention coating and/or encapsulating a compound may be able to withstand the pH of saliva (generally a pH of about 6.5-7.4). In some embodiments, the modified alginate and/or hydrogel may be able to withstand the pH of saliva for a sufficient amount of time such that the modified alginate and/or hydrogel may be able to reach the stomach with at least a portion of the compound (e.g., about 20%, 30%, 40%, 50%, 60%, 70%, 80%, 90%, or 100%) still encapsulated and/or coated. In some embodiments, upon prolonged exposure to the pH of the small intestine, the encapsulated compounds may become bioavailable for their intended benefits.

In some embodiments, a modified alginate of the present invention may be prepared with a method as shown in Scheme VI.

Scheme VI

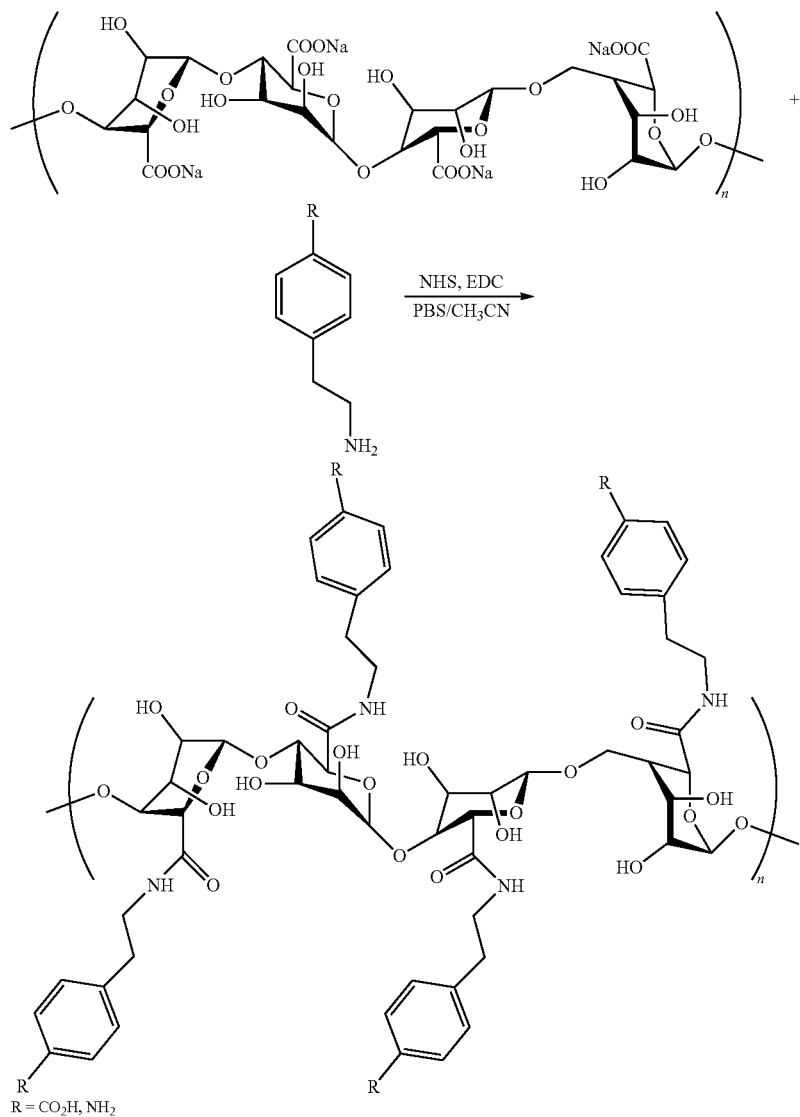

R = CO₂H, NH₂

In some embodiments, to accomplish alginate modification, two approaches may be performed, optionally simultaneously: 1) formation of amide bonds to existing carboxylic acid groups on the alginate backbone and 2) synthesizing small molecules containing catechol functional groups which may be used as modular additives to other available alginate systems. Some of these small molecules may be covalently linked to alginate and some may interact through noncovalent interactions such as hydrogen bonding. In some embodiments, stiffness and/or adhesiveness of a modified alginate may be improved by up to a factor of three with small molecule additives. It has been unexpectedly found that the preparation and/or addition of modular small molecules to alginate using the first approach indicated above may only take a matter of hours, whereas the more classical second approach of forming amide bonds to the polysaccharide first and then using that modified polysaccharide may take days.

In some embodiments, a method of the present invention may allow for incorporation of greater amounts of a reactant (e.g., an aromatic amine such as, e.g., dopamine and/or a pH sensitive compound) into the alginate than has been previously reported and/or compared to different methods. In some embodiments, a method of the present invention may provide about 1% to about 20% or about 5% to about 15% incorporation of a reactant into alginate, wherein the incorporation percentage is based on the average number of polysaccharide units of the alginate. In some embodiments, a reactant (e.g., dopamine) is incorporated into alginate in an amount of about 1%, 2%, 3%, 4%, 5%, 6%, 7%, 8%, 9%, 10%, 11%, 12%, 13%, 14%, 15%, 16%, 17%, 18%, 19%, or 20%. For example, when alginate is prepared containing 4%, 8%, and 13% dopamine incorporation, the modified alginate contains about 1 of every 25 carboxylates modified, 1 of every 12 carboxylates modified, and 1 of every 8 carboxylates modified, respectively.

According to some embodiments of the present invention provided is a cross-linked alginate (e.g., a modified alginate of the present invention that is cross-lined). In some embodiments, the cross-linked alginate is a cross-linked amine modified alginate. The cross-linked alginate may be used for coating and/or encapsulating a bioactive substance (e.g., medicines, drugs, enzymes, proteins, hormones, vaccines, vitamins, minerals, micronutrients and other dietary supplements, biological materials, probiotics and other micro-organisms, and other bioactive compounds and substances).

In some embodiments, a modified alginate of the present invention may be produced using a reaction that does not require elevated temperatures. The techniques disclosed herein may enable application of one or more molecular monolayer(s) of a modified alginate (e.g., an amine modified alginate or dopamine modified alginate) on a bioactive substance, which may provide a coating on the bioactive substance. A monolayer may be on the order of nanometers in thickness. It has been unexpectedly discovered that a compound and/or coating disclosed herein may enable application of a coating and/or encapsulate that can allow a bioactive substance (e.g., various medicines, drugs, enzymes, proteins, hormones, vaccines, vitamins, minerals, micronutrients and other dietary supplements, biological materials, probiotics and other micro-organisms, and other bioactive substances) to be delivered to and used by a host organism, such as humans, optionally without causing premature rupture of the encapsulated material, for example, in the acidic environment of the stomach.

According to some embodiments of the present invention, provided herein is a hydrogel comprising a modified alginate of the present invention. A modified alginate may be present in the hydrogel in an amount of about 0.1% to about 10% w/v of the hydrogel, such as, e.g., about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% w/v of the hydrogel.

The hydrogel may be cross-linked. In some embodiments, the hydrogel is cross-linked with a divalent cation (e.g., calcium). A divalent cation may be present in the hydrogel in an amount of about 0.1 mmol to about 1 mmol. The hydrogel may comprise water or an aqueous solution (e.g., a saline solution) that is optionally buffered.

In some embodiments, the hydrogel comprises a bioactive substance. The hydrogel may coat and/or encapsulate at least a portion (e.g., about 50%, 60%, 70%, 80%, 90%, or 100%) of the bioactive substance. In some embodiments, the bioactive substance is uniformly distributed within the hydrogel.

The hydrogel may have an elastic modulus in a range of 1 or 5 kPa to about 15 or 20 kPa. In some embodiments, the hydrogel is in the form of a bead, capsule (e.g., microcapsule), food product (e.g., edible treat), pellet, and/or hermetically sealed pouch and/or straw. In some embodiments, the hydrogel may be sized for a subject to swallow with or without water. In some embodiments, the hydrogel may have at least one dimension in a range of about 100 microns to about 500 microns or about 200 microns to about 400 microns. In some embodiments, the hydrogel may have at least one dimension that is about 300 microns.

In some embodiments, provided is a biocompatible capsule that comprises a biological material (e.g., a bioactive substance) and a covalently stabilized coating (e.g., a modified alginate coating) which encapsulates the biological material.

In some embodiments, the present invention offers unexpectedly superior properties and/or results because of the modification of alginate such as, e.g., attachment of an amine (e.g., dopamine and/or pH sensitive compound, which may result in enhanced adhesiveness of the alginate.

In some embodiments, covalent modifications of a polysaccharide (e.g., alginate) may alter the acid-base stability of the polysaccharide, which may be used for drug delivery. Amine and/or dopamine modified alginates may be stable in acid environments similar to the stomach environment and a modified alginate (e.g., a modified alginate pellet) may disintegrate readily in a basic environment similar to the small intestine environment. In some embodiments, alginates with varying degrees of amide modification may be provided and/or synthesized, and may be used for acid and base sensitive drug delivery applications. In some embodiments, a modified alginate of the present invention may be formulated into microparticles and/or optimized for acid-base stability. In some embodiments, a modified carbohydrate formulation and/or microparticle of the present invention may be used as a wound healing aid and/or as a surgical adhesive.

In some embodiments, a hydrogel of the present invention may provide a barrier to a bioactive substance (e.g., a medicine, drug, enzyme, protein, hormone, vaccine, vitamin, mineral, and/or micronutrient). The hydrogel may coat at least a portion of the bioactive substance and/or encapsulate at least a portion of the bioactive substance. In some embodiments, a hydrogel of the present invention comprises a bioactive substance (e.g., potassium iodide) and the hydrogel may prevent and/or reduce degradation and/or oxidation of the bioactive substance.

According to some embodiments, a hydrogel of the present invention may increase the shelf life of a bioactive substance when the hydrogel comprises the bioactive substance (e.g., coats and/or encapsulates at least a portion of the bioactive substance). For example, the shelf life of potassium iodide in liquid or powder form may be increased when incorporated in a hydrogel of the present invention. "Shelf life" as used herein refers to the length of time a bioactive substance maintains a given level of activity in an unopened package stored under recommended storage conditions. The shelf life may, for example, be evidenced by the "use by" or "best if used by" date for the product and/or the manufacturer's expiration date of the product (i.e., the "predicted shelf life") and/or the actual product characteristics after the specified period of time (i.e., the "actual shelf life"). Accordingly, the term "shelf life" as used herein should be construed as including both the actual shelf life of the product and the predicted shelf life of the product unless stated otherwise. In some embodiments, shelf life may be determined by extrapolation of data at accelerated temperatures, such as, for example, by using the Arrhenius equation. In some embodiments, shelf life may be determined using linear regression analysis, such as, for example, when the kinetics of the bioactive substance degradation is not temperature dependent. In some embodiments, shelf life may be evaluated and/or determined by measuring the bioactive substance, such as, for example, using high pressure liquid chromatography.

In some embodiments, the shelf life of a hydrogel comprising a bioactive substance is the time that the bioactive substance in the hydrogel maintains at least about 50% (e.g., at least about 50%, 60%, 70%, 80%, 90%, or more) of a given activity (e.g., the ability to deliver and/or provide a therapeutically effect amount of the bioactive substance) compared to the initial activity of the bioactive substance prior to incorporation into the hydrogel. As used herein, the term "therapeutically effective amount" refers to an amount of a bioactive substance and/or hydrogel that elicits a therapeutically useful response in a subject. Those skilled in the art will appreciate that the therapeutic effects need not be complete or curative, as long as some benefit is provided to the subject. In some embodiments, a therapeutically effective amount of a hydrogel of the present invention may include delivering a therapeutically effective amount of a bioactive substance (e.g., potassium iodide) present in the hydrogel.

In some embodiments, a packaged hydrogel of the present invention comprises a bioactive substance (e.g., potassium iodide) and has a shelf life of at least about 1, 2, 3, 4, 5, 6, 7, 8, 9, 10, 11, 12, 13, 14, 15, 16, 17, 18, 19, 20, 21, 22, 23, or 24 months or more, or about 1, 2, 3, 4, 5, 6, 7, 8, 9, 10, 11, 12, 13, 14, 15, 16, 17 years or more, or any range and/or individual value therein.

As used herein, the terms "increase", "improve", and "enhance" (and grammatical variants thereof) refer to an increase in the specified parameter of greater than about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more. As used herein, the terms "decrease", "inhibit", and "reduce" (and grammatical variants thereof) refer to a decrease in the specified parameter of about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%.

Prior to the present invention, to the inventors' knowledge, there was no report of alginate modification by use of amines, or alginate modification such that a hydrogel comprising the modified alginate would readily degrade in response to a basic pH sensitivity and may release encapsulated products (e.g., in the small intestine). Thus, a unique phenomenon that may enhance the bioavailability of therapeutic agents, such as probiotics and other bioactive substances, is contemplated, and therefore within the scope of the present invention.

In an embodiment, the present invention relates to protecting one or more bioactive substances from the destructive effects of an acid and/or an enzyme (e.g., enzymatic action in the stomach), and/or enhancing the bioavailability and/or effectiveness of these bioactive substances by coating and/or encapsulating them in a modified alginate of the present invention, optionally in a hydrogel of the present invention.

In some embodiments, the present invention relates to encapsulating proteins, hormones, and other bioactive substances in a modified alginate of the present invention, which may protect these bioactive substances from attack and/or degradation by an acid and/or an enzyme (e.g., enzymatic action in the stomach). The bioactive substance may be released in the intestines as a modified alginate micro-capsule falls apart and/or diffuses its contents into the intestines. One such example is encapsulating insulin in the modified alginate in a bioavailable form for oral delivery to protect it from destruction by an acid and/or an enzyme (e.g., enzymatic action in the stomach), so that at least a portion of the insulin may be delivered to the small intestine intact, where it may be released and absorbed into the bloodstream for use by humans or other animals in appropriate amounts.

In some embodiments, the present invention relates to encapsulating drugs, medicines, and other bioactive substances in a modified alginate, such as non-prescription pain medications, which may prevent or reduces these substances from causing stomach upset, nausea, and/or vomiting when taken orally. One example is encapsulating aspirin (acetylsalicylic acid) for oral delivery, thereby preventing the release of the acetylsalicylic acid in the stomach, where it often causes stomach upset, nausea, vomiting, and even ulcers (if taken regularly to reduce pain or inflammation). Instead, the encapsulated aspirin is released in the small intestine as the modified alginate micro-capsule falls apart and/or diffuses its contents into the intestines, where it is absorbed into the bloodstream to reduce fever, relieve pain, swelling, and inflammation, from conditions such as muscle aches, toothaches, common cold, flu, headaches, and arthritis; prevent blood clots and lower the risk of heart attack, clot-related strokes and other blood flow problems in patients who have cardiovascular disease, or who have already had a heart attack or stroke; and to treat a variety of other conditions in humans and animals.

In some embodiments, the present invention relates to encapsulating drugs, medicines and other bioactive substances in a modified alginate, such as prescription pain medications, which may prevent or reduce these substances from causing stomach upset, nausea, and/or vomiting when taken orally. An example is encapsulating opioid-based pain medications such as oxycodone, hydrocodone, codeine, morphine, fentanyl and others. These medications often cause stomach upset, nausea, and/or vomiting when taken orally. In some embodiments, when these pain medications are encapsulated in the modified alginate for oral delivery, the modified alginate may prevent and/or reduce the release of the pain medication in the stomach, where it would normally cause stomach upset, nausea, or vomiting. Instead, the encapsulated pain medication may not be released until it reaches the small intestine, where the modified alginate micro-capsule falls apart and/or diffuses its contents into the intestines, where it is absorbed into the bloodstream to reduce moderate to severe pain from a variety of injuries, diseases and other serious or life threatening conditions.

In some embodiments, the present invention relates to encapsulating opioid-based and other potentially addictive pain medications in a modified alginate for oral delivery, which may provide the medication in a form that cannot easily or readily be separated from the modified alginate, turned into a powder, and/or sold by drug dealers to drug addicts, who inhale, snort or smoke the powder, or liquify it and inject it directly into their veins or arteries.

In some embodiments, the present invention relates to encapsulating medicines and other bioactive and therapeutic substances in a modified alginate to increase bioavailability, protect the substance from attack, degradation and/or destruction by an acid and/or an enzyme (e.g., enzymatic action in the stomach), and/or make it largely tasteless, odorless and undetectable for oral delivery to animals, including humans, pets and livestock. The largely tasteless, odorless, and undetectable micro-capsules containing the medicine or other bioactive substance may be combined with pet food, animal feed, and other foodstuffs the animal finds appealing, so that the animal will readily eat the micro-encapsulated medicine or other bioactive substance, and not reject it or spit it out, as is often the case with any food or other substance that does not smell good or taste good to the animal, which also makes it difficult to administer these therapeutic substances to pets, livestock, and other animals. In some embodiments, encapsulation of medicines and other bioactive substances for oral delivery to animals as described herein may (i) increase the bioavailability of the encapsulated medicine or other bioactive substance being ingested, (ii) make it easier to gauge the amount of the bioactive substance that is actually ingested by the animal, (ii) reduce the amount of medicine or other bioactive substance required (dose), since greater bioavailability (i.e., greater efficiency and/or effectiveness of the medicine) often results in a lower dose being required, (iii)

eliminate unnecessary anxiety and/or trust issues between the animal and the person administering the medicine or other therapeutic substance, (iv) eliminate the risk of injuries to persons administering the medicines and other bioactive substances to the animal, and/or (v) eliminate the cost and/or expense of having to utilize a veterinarian or other trained professional to administer the medicine or other bioactive substance to the animal.

In some embodiments, the present invention relates to encapsulating live and/or active probiotics, gut flora, and other "good" or "healthy" micro-organisms in a modified alginate to protect them from attack, degradation, and/or destruction by an acid and/or an enzyme (e.g., enzymatic action in the stomach). The micro-organisms may then be released in the intestines alive and/or intact, where their health and other therapeutic benefits may be fully realized. One example is encapsulating *Lactobacillus Casei* NCDC 298 in a modified alginate. Encapsulating probiotics may increase their shelf-life and/or shield them from attack, degradation, and/or destruction by an acid and/or an enzyme (e.g., enzymatic action in the stomach) after they are orally ingested. When the encapsulated probiotics reach the small intestine, they may be released as the modified alginate falls apart. The probiotics may then be able to recolonize the gut with their "good" bacteria, so that the many health and other therapeutic benefits of the probiotics can be fully utilized and realized. Many other types and strains of probiotics can be encapsulated in a modified alginate for oral delivery to humans and animals.

The maintenance of live bacterial cells until they are able to reach the intestines is one of the key requirements for obtaining health benefits from probiotics. Therefore, in an embodiment, the present invention relates to providing probiotic living cells with a physical barrier against adverse environmental conditions until delivery to the intestines has been accomplished. In some embodiments, the proper conditions are a basic pH. In some embodiments, the present invention relates to a composition that includes an encapsulated probiotic that has a plurality of health benefits.

Because probiotics are biological entities, delivery of sufficient doses is constantly challenged by inherent factors that might limit their biological activity, including the conditions of growth, processing, preservation, and storage. Specifically, loss of probiotic viability occurs at many distinct stages, including freeze-drying of cells during initial manufacturing, during their preparation (high temperature and high pressure), transportation and storage (temperature fluctuations), and after consumption or in gastrointestinal (GI) track (low pH and bile salts). One of the determined factors for probiotics to have beneficial effects is to maintain the high concentration of viable cells for individuals to uptake. Although commercial probiotic products are available, many of them lose their viability during the manufacturing process, transport, storage.

In some embodiments, the present invention relates to a composition which contains a probiotic. In one embodiment, the compositions of the present invention may be good for those that have cardiovascular issues. The composition of the present invention may be useful at improving the immune health of individuals that consume the composition. In one embodiment, the composition of the present invention may comprise both a prebiotic, which may optimize the conditions for any composition, that also contains probiotics.

In some embodiments, a composition of the present invention may contain one or more probiotic cultures that may include, for example, various species of the genera *Bifidobacterium*, *Lactobacillus* and/or propionibacteria such as: *Bifidobacterium animalis lactis*; *Bifidobocterium bifidum*; *Bifidobacterium breve*; *Bifidobacterium infantis*; *Bifidobacterium longum*; *Lactobacillus acidophilus*; *Lactobacillus casei*; *Lactobacillus plantarum*; *Lactobacillus reuteri*; *Lactobacillus rhamnosus*; *Lactobacillus spoogenes* and the like. A species of yeast *Saccharomyces boulardii*, may also be used as a probiotic. In an embodiment, the probiotic cultures include *Bifidobacterium lactis* BI-04, *Bifidobacterium lactis* BB-12 (CHN), and *L. reuteri* (SD 55730—Biogaia).

In an embodiment, the present invention relates to encapsulating vitamins, dietary supplements, and other bioactive substances in a modified alginate for oral delivery to humans and animals, since certain vitamins, dietary supplements, and other bioactive substances suffer from issues of bioavailability, as well as issues of oxidation and the build-up of toxic peroxides and other substances, among other things. These include Omega-3 fatty acids (EPA/DHA), CoQ10, and vitamin D, which current research strongly suggests are important to our overall health and well-being, and should be administered and used to supplement the diets of large numbers of people around the world. Among other things, the bioavailability of these vitamins, dietary supplements, and other bioactive substances, and their ability to be stored for any length of time, are hampered by oxidation and the build-up of toxic peroxides and other substances. They can also be impacted by the intrinsic properties of the digestive tract, especially the differential pH along the tract. The variable pH from the stomach to the intestine impacts the stability, and thereby the bioavailability, of fat and peptide-based dietary supplements and other pharmaceuticals. Some vitamins and dietary supplements, such as vitamin C, vitamin B3, vitamin A and vitamin D, can also cause stomach upset, nausea, and vomiting when taken orally. In some embodiments, when these vitamins, dietary supplements and other bioactive substances are encapsulated in a modified alginate for oral delivery, encapsulation may (i) protect the encapsulated substance from the destructive and/or toxic effects of oxidation while being stored, (ii) prevent or reduce the release of the encapsulated substance in the stomach, where it may cause stomach upset, nausea, or vomiting, (iii) protect the encapsulated substance from attack, degradation, and/or destruction from stomach acids and/or enzymatic action, and/or (iv) prevent at least a portion of the encapsulated substance from being released until it reaches the small intestine, where the micro-capsule may fall apart and/or diffuses its contents into the intestines, where the substance may be absorbed into the bloodstream for its health and other benefits.

One such example is to increase the bioavailability of Vitamin D, which constitutes a largely unrecognized and serious public health problem. Chronic Vitamin D deficiency adversely affects adequate mineralization of bone and leads to rickets in children and osteomalcia or osteoporosis in adults. Low levels of 25-hydroxyvitamin D, the universal clinical parameter of vitamin D status, is associated with an increased risk of cancers, cardiovascular disease, and diabetes, among other diseases. Thus, the present invention relates to methods associated with being able to treat cancers, cardiovascular disease, diabetes, and/or other diseases. In some embodiments, the present invention may address issues that the dietary supplement and/or pharmaceutical industries have long considered necessary, but have been largely unavailable.

In some embodiments, the present invention relates to being able to prolong and/or increase the bioavailability of a bioactive substance (e.g., a medicament/dietary supplement) by combining a bioactive substance that is microencapsulated as described herein with the same or different non-microencapsulated medicament. The medicament/dietary supplement that is not microencapsulated will show bioavailability more rapidly (for example in the acidic stomach) whereas the microencapsulated bioactive substance will not be readily bioavailable until it passes through the acidic stomach. That is, it will be bioavailable once it passes to the more basic conditions of the intestines.

In an embodiment, the present invention relates to encapsulating cells, cell parts, tissues, and other biological materials in a modified alginate in a micro-size suitable for injection, either by itself, or in combination with liposomes, micelles, and/or nanospheres, for targeted delivery to a specific site or group of cells in humans or animals, such as a tumor site.

In embodiments of the present invention, a composition of the present invention may be used to treat one or more maladies. For example, the functional aspects of the invention may act as an antioxidant and/or treat digestive maladies, cognitive disorders, and/or cardiovascular systems and diseases. The formulations of the present invention may be used to treat eczema. In an embodiment, a subject is a human in need of cancer treatment.

In an embodiment, the present invention relates to methods and compositions comprising a hydrogel comprising a modified alginate of the present invention. The hydrogel may be used to micro-encapsulate a bioactive substance. The hydrogel may be administered orally to humans and other animals in order to treat and/or inhibit a wide variety of diseases, parasites, and other conditions without significant degradation of the bioactive substance by stomach acids and/or enzymatic action and/or with reduced negative side effects such as those that accompany certain medicines when taken orally.

In an embodiment, the present formulation may comprise a composition that contains one or more stilbenes sufficient to have desired antioxidant effects. Alternatively, in an embodiment, the one or more stilbenes present may have beneficial anti-inflammatory effects. In some embodiments, the present invention may contain one or more stilbenes that are efficacious in reversing cognitive behavioral deficits. In an embodiment, the formulations of the present invention may be effective against Alzheimer's.

A composition of the present invention may additionally contain pharmaceutically acceptable salts, solvates, and prodrugs thereof, and may contain antiseptics, astringents, diluents, excipients, carriers, micelles, liposomes, and/or other substances necessary to increase the bioavailability and/or extend the lifetime of the compounds/probiotics present in the composition of the present invention. The present invention is not only directed to compositions but is also directed to formulations, supplements, sweeteners, medicaments, and/or other products and methods of using those products, formulations, supplements, and/or medicaments.

In an embodiment, a modified alginate is stable under acidic conditions but is labile under basic conditions. In some embodiments, the modified alginate is stable at a pH of between about 1.5 to 3.5, but is labile when the pH increases above 7. In some embodiments, the modified alginate is stable at a pH of about 3 to 5 and labile at a pH above 7. In some embodiments, the modified alginate is stable for at least about 5, 10, or 15 minutes at a pH above 7. In some embodiments, a modified alginate, optionally in the form of a hydrogel, coats and/or encapsulates a bioactive substance, and has a thickness such that the modified alginate can be exposed to saliva in the mouth and without making the bioactive substance bioavailable until the modified alginate reaches the intestines of an individual administered the modified alginate.

In an embodiment, the present invention relates to a method of making proteins, micronutrients, dietary supplements and/or probiotics more bioavailable to an individual in need of said proteins, micronutrients, dietary supplements and/or probiotics by administering to said individual said proteins, micronutrients, dietary supplements and/or probiotics encapsulated in a modified alginate of the present invention.

In an embodiment, the present invention relates to a method of delivering a dietary supplement or probiotic to an individual in need thereof, said method comprising administering to said individual a composition that comprises a modified alginate of the present invention.

In some embodiments, the present method uses proteins, micronutrients, dietary supplements and/or probiotics that are encapsulated by a modified alginate of the present invention.

In an embodiment, the present invention relates to a method of treating an individual in need thereof by administering proteins, micronutrients, dietary supplements and/or probiotics to said individual, wherein the proteins, micronutrients, dietary supplements and/or probiotics are encapsulated in a modified alginate, the modified alginate being modified as described above. The method may include treating individuals for depression wherein the method uses as a dietary supplement fish oil that serves as a primary source for omega-3 fatty acids. The method may boost the ability to boost the effects of antidepressants, they also may aid in treating the depressive symptoms of bipolar disorder. The method may be also used for treating visual or neurological problems in infants or aiding visual and neurological development in infants. The method may allow ingestion of omega-3 fatty acids in relatively high doses that may lower inflammation, and may treat asthma.

In an embodiment, the invention relates to delivering omega-3 fatty acids to individuals, which are useful in ameliorating and/or reducing symptoms associated with ADHD in some children, while at the same time enhancing their mental skills. The invention also relates to the use of omega-3 fatty acids to treat or slow the progression of Alzheimer's disease and/or dementia.

In an embodiment, the invention relates to a method of using a modified alginate to deliver vitamin D. Thus, the method may be used to reduce inflammation (by acting on C-Reactive Protein). In some embodiments, the method of delivering vitamin D may aid individuals in reducing pain as well as the stress on joints. The method may also relate to the treatment of or reducing rheumatoid arthritis, obesity, certain cancers, various heart diseases, and the effects of radiation. Similarly, the method may be used to enhance individuals' mental capacity, the immune system, bone growth, and the proper production of insulin.

In an embodiment, the present invention relates to a method of administering insulin by using the methods and compositions as disclosed above. Thus, the method may be used as a means of keeping the blood sugar level from getting too elevated (hyperglycemia) or too low (hypoglycemia). In a variation, the method may be able to aid individuals who are unable to effectively produce the correct amount of insulin.

In an embodiment, the present invention also relates to a method of treating irritable bowel syndrome that allows the modified alginate to encapsulate a medicament that enhances the bioavailability of the medicament in the intestines where the medicament is most needed. Moreover, this would allow the delivery of medicaments that otherwise might be acid labile (that is, these medicaments are able to survive the acidic conditions of the stomach because they are encapsulated).

In an embodiment, 8% dopamine-modified alginate (DMA) was tested to make slabs encapsulating nanoparticles for oral drug delivery. After 2% weight % DMA was dissolved in Hank's Balanced Salt Solution (HBSS) without calcium, Omega-3 oil loaded silica nanoparticles were mixed with the DMA. The mixture was then crosslinked by adding $CaCl_2$ and allowed to sit for about 15 minutes at room temperature until it formed a hydrogel slab. The hydrogel was cut in half to compare the degradation rate in different pH environments. One-half of the hydrogel was placed in a 1 N HCl (pH<1), and the other in a bath of Krebs Ringer Solution (pH 7.4) to mimic the highly acidic stomach, and the more neutral gut conditions, respectively. The hydrogel slabs under these two conditions were placed in an incubator at 37° C. and an inverted light microscope was used to compare the overall shape, transparency, and release of nanoparticles from the two incubation conditions. Images of the slabs were taken initially, at 1.5 hours and after overnight incubation it was apparent that the neutral pH caused the DMA hydrogel to degrade rapidly, thereby releasing the nanoparticles into the bath. The hydrogel that was placed in the acidic bath remained intact for an additional 2 weeks of follow up.

In some embodiments, microbeads comprising a modified alginate and a bioactive substance may be used to delay the transit time of the beads in the intestine such that sustained delivery of the bioactive substance may be achieved and/or enhanced therapeutic efficacy. In some embodiments, increased stability of the modified alginate microbeads may be achieved by increasing the degree of modification of alginate with the reactant (e.g., dopamine).

The following are examples of procedures used to micro-encapsulate certain identified bioactive substances with a modified alginate of the present invention. These examples are illustrative only and are not to be considered the only embodiments of the invention.

Alginate Micro-Encapsulation Procedures

The following procedures can be used to micro-encapsulate any of a plurality of bioactive substances.

Modified alginate is dissolved in Hanks Balanced Salt Solution (HBSS) (Sigma) overnight at 4° C. The desired compounds, drugs, or cells are suspended in the alginate and mixed to ensure uniform distribution of the various substances. The suspensions are then loaded into a peristaltic pump, extruded through a 15-gauge needle at a rate of 0.2 ml/min, and droplets of the suspension are received in a bath of calcium chloride ($CaCl_2$) for crosslinking (gelation). The crosslinked microbeads are then collected and washed twice with HBSS supplemented with 25 mM $CaCl_2$.

Effects of Alginate Modification

Two methods are described below for modifying the alginate, each of which determines how the alginate will degrade in more neutral pH solutions. A first method for modifying the alginate degrades slower relative to a second method for modifying the alginate, which can be useful for targeted delivery in the gastrointestinal tract (GIT). The second method has been shown to result in alginate microbeads that fall apart (degrade) within 30 minutes, while microbeads generated from alginate modified by the first method degrade in about 1-2 hours. The two methods are as follows:

Method 1:

Alginate (1 mmol equivalent) is dissolved in about 25 mL of premade phosphate buffer solution (pH 6.0) and 25 mL of acetonitrile. 1.1 mol equivalent of EDC (1-Ethyl-3-(3-dimethylaminopropyl)carbodiimide) and 1.5 mol equivalent of NHS (N-Hydroxysuccinimide) are added to the solution. The reaction is stirred for 1 h in the dark followed by addition of 1.8 equivalent of 4(2-ethylamino) benzoic acid-.HCl. The mixture is stirred in the dark under inert atmosphere for the next 18 h. The solution is then dialyzed for 12 h in 0.1M NaCl and then deionized water for 24 h. The solvent is then removed via lyophilization. 210 mg of white, cotton textured modified alginate material was obtained.

Method 2:

The alginate (1 mmol equivalent) is dissolved in ultrapure water (Millipore Sigma) with 10% (v/v) isopropanol to about 8 mg/mL. The solution is degassed with $N_2$ and chilled to about 2-4 □C. A degassed solution of sodium (meta) periodate (0.25M solution) is added based on the desired degree of oxidation intended (at 0.5% oxidation). The mixture is stirred for 48 h in the dark and then dialyzed in ultrapure water until the conductivity was below 2 μS and then dried via lyophilization.

The periodate oxidized alginate is dissolved in ultrapure water and methanol (12% v/v). Equivalent moles of amine substituent are added to the solution matching the % oxidized alginate and about 10 mol equivalent of pic-$BH_3$ (2-picoline-borane). The pH of the mixture is adjusted to about pH 6 using phosphate buffer and the solution is stirred in the dark for 24 h. The sample is dialyzed in 0.1 M NaCl for 12 h followed by dialysis in ultrapure water for 24 h and then lyophilized.

Substituent presence and modification quantification was done via quantitative $^1$H NMR using 3-(trimethylsilyl)-2,2,3,3-tetradeuteratedpropionic acid sodium salt (TMSP-d4) as an internal standard.

Diffusion-Ordered Spectroscopy (2D-DOSY—Linear gradient) was acquired to confirm the covalent bonding of the substituent to the alginate polymer.

Additional Modifications

Two additional parameters can be changed to further modify the degradation rate of the modified alginate. They are: (1) the type of alginate used, and (2) the alginate concentration. Both LVM (low viscosity mannuronic acid) and LVG (low viscosity guluronic acid) alginate are commonly used for encapsulation, but LVG creates a stronger hydrogel network which slows down the degradation of the modified alginate. Also, increasing the concentration of alginate creates a denser network which slows down the degradation rate. Each of these variables can be adjusted or combined to create a targeted delivery system for the desired compound depending on the mammalian species involved and where and when to deliver the compound of interest.

The following more specific examples are illustrative of several of the useful embodiments of the present invention. Procedures for Micro-Encapsulating Dewormer Drugs/Medications As one example of micro-encapsulating dewormer medications for horses, cattle, sheep, dogs, cats, and other animals, the equine deworming drug Benzimidazole can be micro-encapsulated in the Modified Alginate. Benzimidazole is approximately 118.14 g/mol. in powder form. The procedure is as follows.

The Benzimidazole should be mixed with the Modified Alginate at approximately 20% w/v (20 g/100 mL). The suspension can then be loaded into a peristaltic pump, extruded through a 15-gauge needle at a rate of approximately 0.2 mL/min, and droplets of the suspension are received in a bath of calcium chloride ($CaCl_2$) for crosslinking (gelation). The crosslinked microbeads are then collected and washed twice with HBSS (Hanks Balanced Salt Solution) supplemented with 25 mM $CaCl_2$. There will be approximately $1.693*10^{-3}$ mol of Benzimidazole in the 1 mL of alginate.

By encapsulating approximately 0.2 g of powder per 1 mL of the Modified Alginate, approximately 40 micro-beads containing the specified amount of Benzimidazole are produced.

Procedures for Micro-Encapsulating ADHD Medications

As one example of micro-encapsulating ADHD medications, the medication Methylphenidrate can be micro-encapsulated in the Modified Alginate. Methylphenidrate has a molecular weight of 233.31 g/mol in powder form. The procedure is as follows.

The Methylphenidrate is mixed with the alginate at 20% w/v (20 g/100 mL). The suspension is then loaded into a peristaltic pump, extruded through a 15-gauge needle at a rate of 0.2 mL/min, and droplets of the suspension are received in a bath of calcium chloride ($CaCl_2$) for crosslinking (gelation). The crosslinked microbeads will then be collected and washed twice with HBSS supplemented with 25 mM $CaCl_2$. There will be approximately $8.572*10^{-3}$ mol of Methylphenidrate in the 1 mL of alginate.

Procedures for Micro-Encapsulating Prescription Pain Medications

As one example of micro-encapsulating prescription pain medications, Oxycodone can be micro-encapsulated in the Modified Alginate. Oxycodone has a molecular weight of 315.364 g/mol in powder form. The procedure is as follows.

The Oxycodone can be mixed with the alginate at 20% w/v (20 g/100 mL). The suspension is then loaded into a peristaltic pump, extruded through a 15-gauge needle at a rate of 0.2 mL/min, and droplets of the suspension are received in a bath of calcium chloride ($CaCl_2$) for crosslinking (gelation). The crosslinked microbeads will then be collected and washed twice with HBSS supplemented with 25 mM $CaCl_2$. There will be approximately $6.34*10^{-4}$ mol of Oxycodone in the 1 mL of alginate.

Procedures for Micro-Encapsulating Probiotics

As one example of micro-encapsulating probiotics, the probiotic *Lactobacillus Casei* NCDC 298 can be micro-encapsulated in the Modified Alginate. The procedure is as follows.

The *Lactobacillus* is cultured overnight in MRS broth then spun down and mixed with the alginate. The suspension is then loaded into a peristaltic pump, extruded through a 15-gauge needle at a rate of 0.2 ml/min, and droplets of the suspension are received in a bath of calcium chloride ($CaCl_2$) for crosslinking (gelation). The crosslinked microbeads are then collected and washed twice with HBSS supplemented with 25 mM $CaCl_2$. There will be approximately $40.0*10^9$ lactobacilli in the 1 mL of alginate.

Procedures for Micro-Encapsulating Dietary Supplements

As one example of micro-encapsulating dietary supplements, Vitamin E (alpha-tocopherol acetate) can be micro-encapsulated in the Modified Alginate. Alpha-tocopherol acetate has a molecular weight of 472.743. The procedure is as follows.

The alpha-tocopherol acetate is mixed with the alginate at 20% w/v (20 g/100 mL). The suspension is then loaded into a peristaltic pump, extruded through a 15-gauge needle at a rate of 0.2 mL/min, and droplets of the suspension are received in a bath of calcium chloride ($CaCl_2$) for crosslinking (gelation). The crosslinked microbeads will then be collected and washed twice with HBSS supplemented with 25 mM $CaCl_2$. There will be approximately $4.23*10^{-4}$ mol of Vitamin E in the 1 mL of alginate.

Procedures for Micro-Encapsulating Selective Serotonin Reuptake Inhibitors (SSRIs)

As one example of micro-encapsulating Selective Serotonin Reuptake Inhibitors, Paroxetine (Paxil) can be micro-encapsulated in the Modified Alginate. Paroxetine has a molecular weight of 374.83 g/mol in powder form. The procedure is as follows.

The Paroxetine is mixed with the alginate at 20% w/v (20 g/100 mL). The suspension is then loaded into a peristaltic pump, extruded through a 15-gauge needle at a rate of 0.2 mL/min, and droplets of the suspension are received in a bath of calcium chloride ($CaCl_2$) for crosslinking (gelation). The crosslinked microbeads will then be collected and washed twice with HBSS supplemented with 25 mM $CaCl_2$. There will be approximately $5.33*10^{-4}$ mol of Paroxetine in the 1 mL of alginate.

Procedures for Micro-Encapsulating Non-Prescription Pain Medications

As one example of micro-encapsulating non-prescription pain medications, Acetylsalicylic Acid (Aspirin) can be micro-encapsulated in the Modified Alginate. Acetylsalicylic Acid has a molecular weight of 180.157 g/mol in powder form. The procedure is as follows.

Acetylsalicylic Acid is mixed with the alginate at 20% w/v (20 g/100 mL). The suspension is then loaded into a peristaltic pump, extruded through a 15-gauge needle at a rate of 0.2 mL/min, and droplets of the suspension are received in a bath of calcium chloride ($CaCl_2$) for crosslinking (gelation). The crosslinked microbeads will then be collected and washed twice with HBSS supplemented with 25 mM $CaCl_2$. There will be approximately $1.11*10^{-3}$ mol of Acetylsalicylic Acid in the 1 mL of alginate.

Procedures for Micro-Encapsulating Potassium Iodide

Potassium iodide can be micro-encapsulated in the Modified Alginate as a powder and/or as a liquid. Potassium iodide has a molecular weight of 166.0 g/mol in powder form. The procedure can be as follows.

Potassium iodide (KI) in powder form is mixed with an alginate in an amount of 20% w/v (20 g of KI/100 mL of alginate) to form a suspension. The suspension is then loaded into a peristaltic pump, extruded through a 15-gauge needle at a rate of 0.2 mL/min, and droplets of the suspension are received in a bath of calcium chloride ($CaCl_2$) for crosslinking (gelation). The crosslinked microbeads will then be collected and washed twice with HBSS supplemented with 25 mM $CaCl_2$. There will be approximately $1.20 \times 10^{-3}$ mol of potassium iodide in 1 mL of alginate.

Liquid potassium iodide can be loaded into alginate beads of the present invention using a soaking method. The procedure is as follows. Alginate is loaded into a peristaltic pump, extruded through a 15-gauge needle at a rate of 0.2 mL/min, and droplets of the liquid are received in a bath of calcium chloride ($CaCl_2$) for crosslinking (gelation). The crosslinked microbeads will then be collected and washed twice with HBSS supplemented with 25 mM $CaCl_2$. Then, the beads will be soaked in a bath of potassium iodide for about 24 hours. Excess fluid will be aspirated and the beads are allowed to air dry, and then they are ready for use.

According to embodiments of the present invention provided are oral delivery systems for medicines and/or other substances in humans and other animals. The methods of the present invention may be advantageous in that they may provide: (1) protection of the encapsulated substance from destruction and/or degradation by stomach an acid and/or an enzyme (e.g., enzymatic action in the stomach), (2) the elimination and/or reduction of stomach upset, nausea, and/or vomiting caused by certain medicines and other substances when they are introduced into the stomach, (3) a resulting increase in the bioavailability of the substance when it reaches the small intestine, where the contents of the micro-capsule are released into the small intestine through the process of diffusion, or its contents are fully released when the micro-capsule breaks apart in the small intestine due to the pH differential between the stomach and the small intestine, (4) a reduction in the dosage required, since the overall bioavailability of the substance has been increased, (5) the ability to control the rate of release of the substance as it passes through the small intestine by adjusting the chemistry of the aromatic/carbohydrate combination, thereby increasing or decreasing the sensitivity of the micro-capsule material to the PH differential, (6) the ability to completely hide or mask the real taste or flavor of the medicine or substance in the micro-capsule for easier administration of unpleasant or noxious tasting substances to humans and animals, (7) the ability to add the micro-encapsulated substance to existing desirable foods or "treats," so the medicine or other substance can be consumed readily by humans or animals undetected, and/or (8) the ability to suspend the micro-encapsulated substance in liquids for easier administration to humans (particularly children) and certain animals.

The present invention has a plurality of uses including, but not limited to, the ability to deliver medicines, drugs, chemicals, proteins, enzymes, probiotics, dietary supplements, and other bioactive substances to humans and other animals, which can be used to treat and/or inhibit diseases, parasites, and/or other conditions in the humans and other animals, eliminate or reduce pain associated with a wide variety illnesses, diseases and conditions, and/or maintain the good health and well-being of humans and other animals, including, but not limited to, the following classes or categories of medicines and other bioactive substances:

(a) Oral agents including sulfonylureas, insulin-sensitizers, and insulin;
(b) Anticancer drugs and chemotherapeutic agents;
(c) Neuroleptics and antipsychotic drugs, tranquillizers, antidepressants and sedatives;
(d) Antibiotics and antimicrobials;
(e) Antiepileptic and anticonvulsant drugs;
(f) Neurotransmitters;
(g) Anti-hypertensives such as beta blockers and ACE-inhibitors; and
(h) Statins including Lipitor and Zocor, among others.

Pain Medications

The present invention may be used to eliminate or reduce pain and/or inflammation by administering one or more of the following classes of pain medications to humans and animals without encountering certain negative side effects:

1. Non-prescription pain medications, such as nonsteroidal anti-inflammatory drugs, including, but not limited to, aspirin (acetylsalicylic acid), ibuprofen, naproxen, and any combinations thereof.

2. Prescription pain medications, such as nonsteroidal anti-inflammatory drugs, including, but not limited to, fenoprofen, flurbiprofen, ketoprofen, oxaprozin, diclofenac sodium, etodolac, indomethacin, ketorolac, sulindac, tolmetin, meclofenamate, mefenamic acid, nabumetone, piroxicam, and any combinations thereof.

3. Prescription pain medications, such as opioid drugs, including, but not limited to, codeine, fentanyl, hydrocodone, hydrocodone with acetaminophen, hydromorphone, meperidine, methadone, morphine, oxycodone, tapentadol, oxymorphone, buprenorphine, tramadol, oxycodone with acetaminophen, naloxone, and any combinations thereof.

Probiotics

The present invention may be used to deliver live probiotics and/or other beneficial micro-organisms to humans and animals for their therapeutic benefits, such as:

1. Probiotic strains and other micro-organisms found in or beneficial to the human microbiome, including, but not limited to:

(a) Probiotic Strains of the *Lactobacillus* species of bacterium, including, but not limited to, *L. acidophilus, L. fermentum, L. plantarum, L. rhamnosus, L. salivarius, L. paracasei, L. gasseri, L. brevis, L. bulgaricus, L. caucasicus, L helveticus, L. lactis, L. casei,* and *L. reuteri,* and any combination thereof.

(b) Probiotic Strains of the *Bifidobacterium* species of bacterium, including, but not limited to, *B. bifidum, B. longum,* and *B. infantis,* and any combination thereof.

(c) Probiotic strains of the *Bacillus* species of bacterium, including, but not limited to, *B. coagulans,* and any combination thereof.

(d) Probiotic strains of the Streptoccocus species of bacterium, including, but not limited to, *S. salivarius* K12, and S. *Salivarius* M18, and any combination thereof.

(e) Other probiotic strains of bacterium found in or beneficial to the human microbiome, including, but not limited to, probiotic strains of bacterium used to treat or combat *Clostridium difficile* (*C. diff.*), as well as other intestinal diseases or conditions, and any combination thereof.

2. Probiotic strains of bacterium found in or beneficial to the microbiome of other animals, including, but not limited to, dogs, cats, horses, cattle, sheep, pigs, chickens, and includes any combination of those probiotic strains of bacterium.

Dietary Supplements

The invention may be used to deliver vitamins, minerals, micro-nutrients, and/or other dietary supplements to humans and animals protected from oxidation and without certain negative side effects, such as:

1. Dietary supplements, including, but not limited to, omega-3 fatty acids (EPA/DHA), vitamin D, vitamin B1, B2, B3, B5, B6, B7, B9, B12, B17, vitamin B complex, alpha lipoic acid, and Coenzyme Q10, among others, and any combinations thereof.

Equine Dewormers

In an embodiment, the invention can be used to deliver deworming medicines and other bioactive substances to horses, such as:

1. Medicines and other bioactive substances used to treat, prevent, inhibit, and/or remove gastrointestinal parasites in horses, such as Strongyles (blood or red worms, including *S. vulgaris, S. edentates,* and *S. equinus*), *Ascarids* (roundworms), Tapeworms, and Bots. These medicines and other bioactive substances include, but are not limited to, Benzimidazoles (including the generics Fenbendazole and Oxibendazole), Macrocyclic Lactones (including the generics Ivermectin and Moxidectin), Tetrahydropurimidines (including the generics Pyrantel Pamoate and Pyrantel Tatrate), and Isquinoline-pyrozines (including the generic Praziquantel), and any combinations thereof.

2. Medicines and other bioactive substances used to treat, prevent, and/or inhibit other diseases and conditions in horses, reduce pain and inflammation, and maintain their general health and well-being.

Feline and Canine Dewormers

In an embodiment, the invention can be used to deliver deworming medicines and other bioactive substances to dogs and cats, such as the delivery of:

1. Medicines and other bioactive substances used to treat, inhibit, and/or remove gastrointestinal parasites in cats, including, but not limited to, Piperazine, Praziquantel, Ivermectin, Selamectin, Imidacloprid, Moxidectin, and any combination thereof.

2. Medicines and other bioactive substances used to treat, inhibit, and/or remove gastrointestinal parasites in dogs, including, but not limited to, Pyrantel pamoate, Praziquantel, Fenbendazole, Ivermectin, Milbemycin oxime, Selamectin, Imidacloprid, Moxidectin, Spinosad, and any combination thereof.

3. Medicines and other bioactive substances used to treat, prevent, and/or inhibit other diseases and conditions in cats and dogs, reduce pain and inflammation, and maintain their general health and well-being.

Dewormers Used in Other Animals

In an embodiment, the invention can be used to deliver deworming medicines to other animals, such as:

1. Medicines and other bioactive substances used to treat, inhibit, and/or remove gastrointestinal parasites in other animals, such as cattle, sheep, and pigs, including, but not limited to, Fenbendazole, Ivermectin, Levamisole, Morantel tartrate, Thiabendazole, Albendazole, Oxfendazole, and any combination thereof.

Treating and/or Inhibiting Diseases and Conditions in Other Animals

In an embodiment, the invention can be used to deliver medicines and other bioactive substances to animals such as:
1. Medicines and other bioactive substances used to remove parasites, treat, prevent, and/or inhibit diseases and other conditions, reduce pain or inflammation, and maintain their general health and well-being.

Rodenticides

In an embodiment, the invention can be used to deliver rodenticides to rodents such as:

1. Chemicals, drugs, compounds, and other substances used to eliminate and/or control rodents or rodent populations, including, but not limited to, Warfarin, Chlorphacinone, Diphacinone, Bromadiolone, Difethialone, Brodifacoum, Bromethalin, Cholecalciferol, Zinc phosphide, Strychnine, triptolide, 4-vinylcyclohexene diepoxide, diterpenoid epoxides, ovotoxins, diterpenoid epoxides, and any combinations thereof.

EXAMPLES

Example 1

We have prepared amide modifications of alginate using a literature preparation (Follain, N., Montanari, S., Jeacomine, I., Gambarelli, S. & Vignon, M. R. Coupling of amines with polyglucuronic acid: Evidence for amide bond formation. *Carbohydrate Polymers* 74, 333-343 (2008)) and have developed a $^1$H NMR method for quantifying the degree of incorporation of the various amine compounds into the alginate backbone. Scheme VII shows one amide bond formation in compound 33 for the purposes of illustration. We have also used the NHS/EDC preparative method (Yang, J.-S., Xie, Y.-J. & He, W. Research progress on chemical modification of alginate: A review. *Carbohydrate Polymers* 84, 33-39 (2011)) to initially prepare alginate containing 4-(2-aminoethyl)-benzoic acid at 0.04 to 0.4% amine incorporation and have used a literature periodate alginate oxidation/amidation method (Dalheim, M. Ø. et al. Efficient functionalization of alginate biomaterials. *Biomaterials* 80, 146-156 (2016)) to achieve amine incorporations>5%. To characterize these new materials such as 33, we first use HMBC (600 MHz with cryo-probe) to verify a through bond connection from the benzylic $CH_2$ to a carbonyl. The same carbonyl has alginate protons correlated within three bonds as well. This data is consistent with a covalent connection between the alginate and aminoethyl benzoic acid modifier. In addition to this HMBC data, we have performed 2D DOSY experiments (linear gradient) showing the alginate and aminoethyl benzoic acid modifier within a narrow band of diffusion orders. Free modifier in alginate versus covalently bonded modifier clearly gives different diffusion orders. A squared gradient DOSY processed with a direct exponential curve resolution algorithm (DECRA)[67] showed this same sample to contain 93% covalently bonded aminoethyl benzoic acid and 7% noncovalently bonded modifier.

Scheme VII

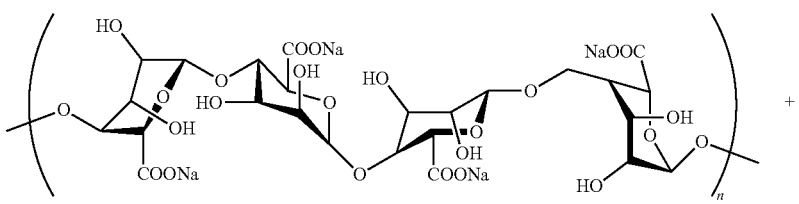

31

-continued

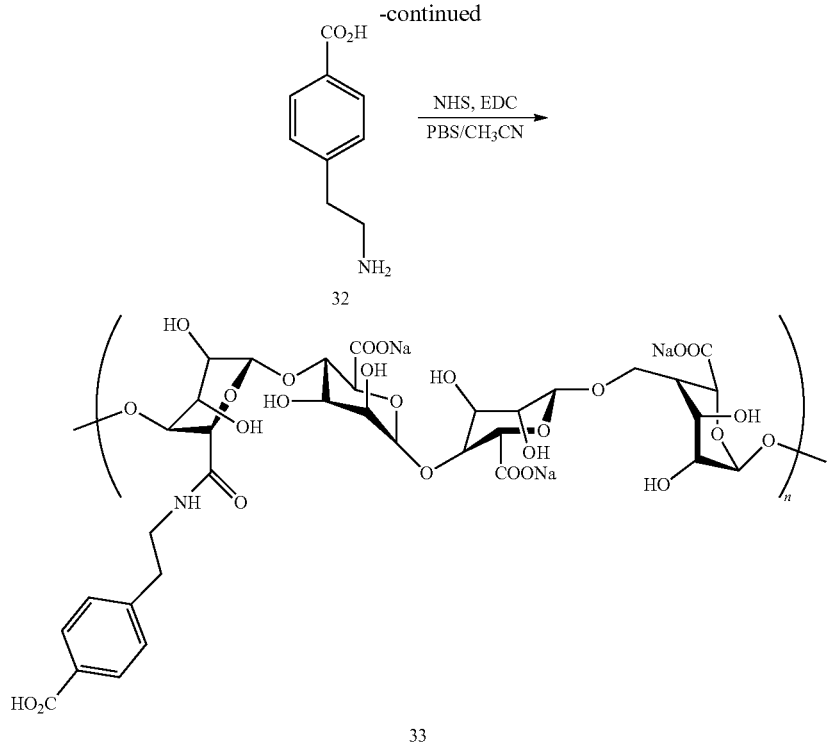

Following preparation of these materials, the acid-base sensitivities of hydrogel microbeads of the modified alginates were tested. After modification of ultrapure low-viscosity high-mannuronic acid (LVM) alginate (Novamatrix, Sandvika, Norway) by 0.042% 4-(2-aminoethyl) benzoic acid, microspheres of either unmodified (control) or the modified alginate were generated using a microfluidic approach (Tendulkar, S. et al. A three-dimensional microfluidic approach to scaling up microencapsulation of cells. *Biomedical Microdevices* 14, 461-469 (2012)). The alginate microspheres were gelled by calcium crosslinking and each of the two groups of microbeads had one aliquot incubated in different media to mimic the highly acidic stomach (pH<3), and another aliquot in a bath of simulated small intestinal fluid (pH>6.8) to mimic the neutral-basic pH gut conditions of this region.

Figure 2:
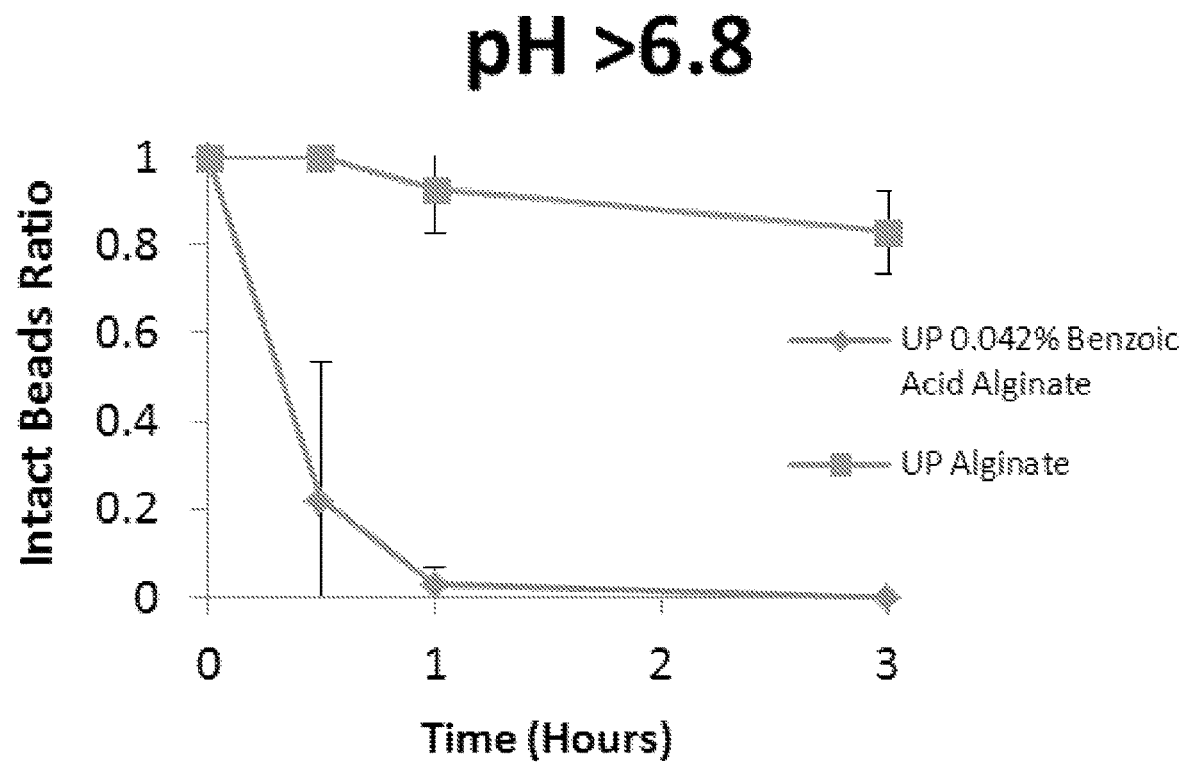
FIG. 2 shows a graph of the stability of unmodified and benzoic acid-modified alginate under neutral-basic pH condition (pH 6.8).
Figure 3:
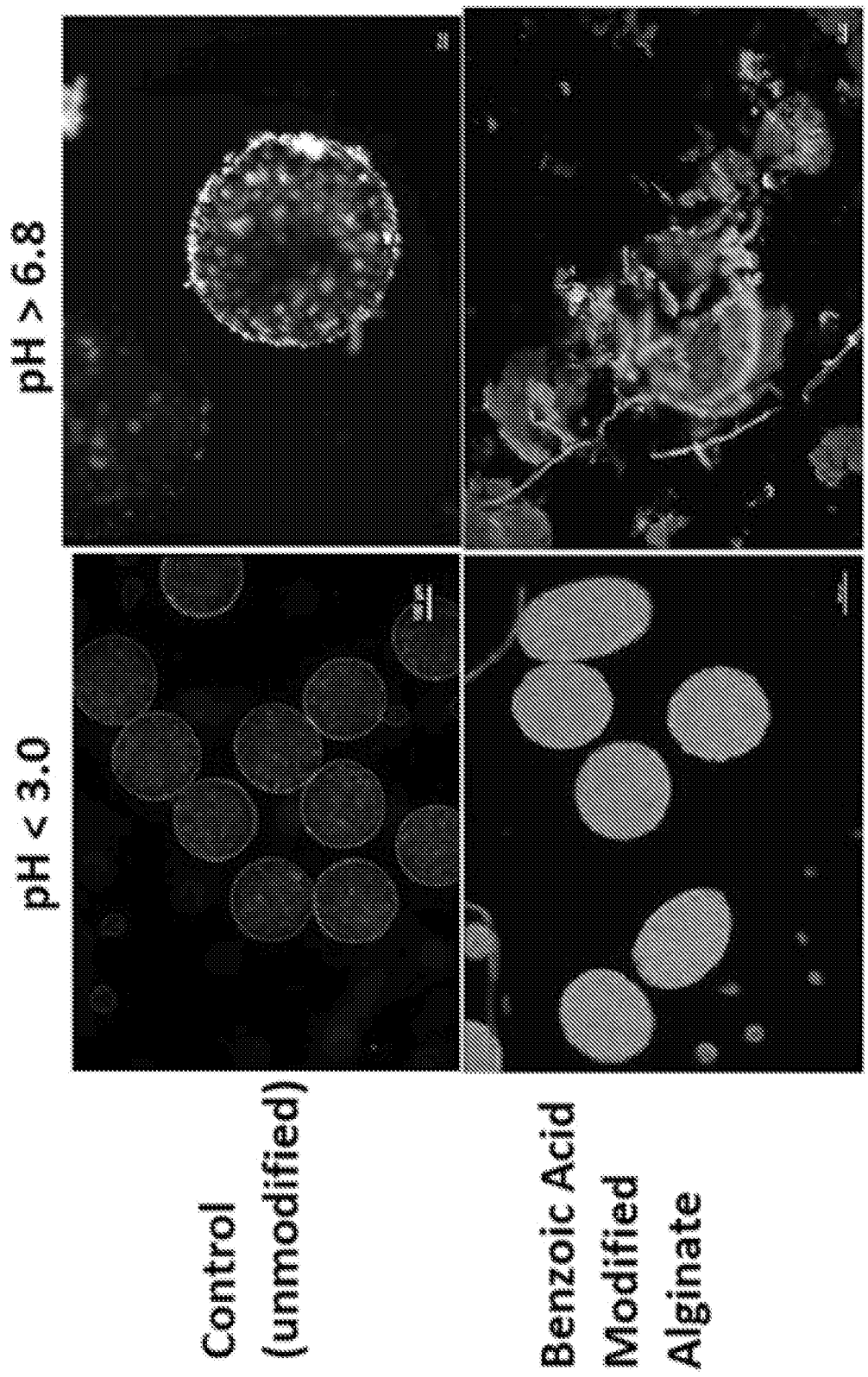
FIG. 3 shows images of modified alginate materials under acid versus neutral-basic pH conditions.

As shown in FIG. 1, while the microbeads made with the unmodified alginate remained stable during a 3-hour incubation under both acidic and neutral pH conditions, those made with the modified alginate while resistant to acidic conditions, disintegrated under the neutral-basic conditions. FIG. 2 shows the decay curve of the modified alginate over the 3 hours of incubation under the neutral-basic pH conditions during which the unmodified alginate microbeads largely remained intact. FIG. 3 shows that both the modified and unmodified alginate microbeads were equally stable during the 3-hour incubation in acidic pH. These data clearly shows that even a low degree of benzoic acid modification of alginate results in apparent neutral-basic pH-sensitivity of the hydrogel microbeads consistent with observations by other investigators with a calcium-alginate/protamine shell carrier (Mei, L. et al. Novel Intestinal-Targeted Ca-Alginate-Based Carrier for pH-Responsive Protection and Release of Lactic Acid Bacteria. *ACS Applied Materials & Interfaces* 6, 5962-5970 (2014)).

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed:

1. A compound comprising at least one unit having a structure of Formula I:

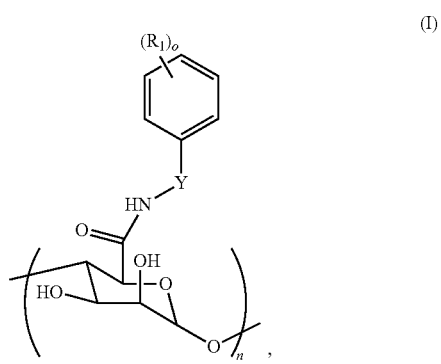

wherein
Y is absent or a $C_1$-$C_4$ alkyl or $C_1$-$C_4$ alkenyl;
$R_1$ is each independently selected from the group consisting of —H, —OH, —NH$_2$, —COOH, —NO$_2$, —CN, —Br, —Cl, —F, —$C_1$-$C_6$ alkylhalide, unsubstituted or substituted —$C_1$-$C_6$ alkyl, unsubstituted or substituted —$C_1$-$C_6$ alkenyl, —SO$_2$H, —SO$_3$H, —COCH$_3$, —Si (OH)₃, —SO₂NH₂, —PO(OR')₂, and —B(OH)₂, wherein R' is unsubstituted or substituted alkyl, alkenyl, alkynyl, or aryl;

n is from 1 to 1,000,000; and o is 1, 2, 3, 4, or 5, wherein at least one R₁ is in the para position and is selected from the group consisting of —NH₂, —COOH, —NO₂, —CN, —Br, —Cl, —F, —C₁-C₆ alkylhalide, unsubstituted or substituted —C₁-C₆ alkyl, unsubstituted or substituted —C₁-C₆ alkenyl, —SO₂H, —SO₃H, —COCH₃, —Si(OH)₃, —SO₂NH₂, —PO(OR')₂, and —B(OH)₂, and wherein R' is unsubstituted or substituted alkyl, alkenyl, alkynyl, or aryl, and wherein the compound is an alginate polymer.

2. A compound comprising at least one unit having a structure of Formula II:

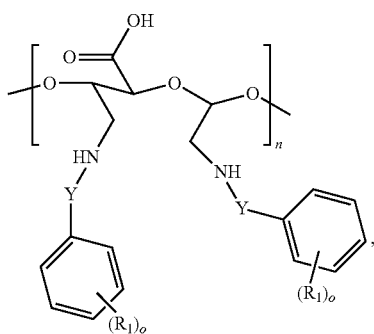

(II)

wherein

Y is absent or a C₁-C₄ alkyl or C₁-C₄ alkenyl;

R₁ is each independently selected from the group consisting of —H, —OH, —NH₂, —COOH, —NO₂, —CN, —Br, —Cl, —F, —C₁-C₆ alkylhalide, unsubstituted or substituted —C₁-C₆ alkyl, unsubstituted or substituted —C₁-C₆ alkenyl, —SO₂H, —SO₃H, —COCH₃, —Si(OH)₃, —SO₂NH₂, —PO(OR')₂, and —B(OH)₂, wherein R' is unsubstituted or substituted alkyl, alkenyl, alkynyl, or aryl;

n is from 1 to 1,000,000; and o is 0, 1, 2, 3, 4, or 5, and wherein the compound is an alginate polymer.

3. The compound of claim 1, wherein at least one R₁ has a pKa in a range of about 3 to about 6.

4. The compound of claim 1, wherein the compound comprises at least one pH sensitive functional group.

5. The compound of claim 1, wherein the compound is prepared by reacting alginate with a reactant.

6. The compound of claim 5, wherein the alginate is an oxidized alginate.

7. The compound of claim 5, wherein the reactant is incorporated into the alginate in an amount of about 1% to about 15% of the polysaccharide units of the alginate.

8. The compound of claim 5, wherein at least 90% of the reactant is chemically bonded to the alginate.

9. A hydrogel comprising the compound of claim 1, wherein the compound is present in the hydrogel in an amount of about 0.1% to about 10% w/v of the hydrogel.

10. The hydrogel of claim 9, wherein the hydrogel is cross-linked.

11. The hydrogel of claim 9, wherein the hydrogel further comprises a bioactive substance.

12. The hydrogel of claim 11, wherein the bioactive substance is uniformly distributed within the hydrogel.

13. The hydrogel of claim 9, wherein the hydrogel further comprises a divalent cation in an amount of about 0.1 mmol to about 1 mmol.

14. The hydrogel of claim 9, wherein the hydrogel has an elastic modulus in a range of 1 kPa to about 20 kPa.

15. The hydrogel of claim 9, wherein the hydrogel is in the form of a bead, microcapsule, and/or pellet.

16. A method of treating a subject, the method comprising administering the hydrogel of claim 9 to a subject, wherein the hydrogel comprises at least one bioactive substance, thereby treating the subject.

17. A method of increasing the stability and/or shelf life of a bioactive substance, the method comprising providing a hydrogel of claim 9, wherein the hydrogel comprises at least one bioactive substance, thereby increasing the stability and/or shelf life of the bioactive substance.

18. The compound of claim 2, wherein o is 5 and each R₁ is —H.

19. The compound of claim 2, wherein o is 1, 2, 3, 4, or 5 and at least one R₁ is an unsubstituted or substituted C₁-C₆ alkyl.

20. The compound of claim 2, wherein o is 1, 2, 3, 4, or 5 and at least one R₁ is —COCH₃.

* * * * *

UNITED STATES PATENT AND TRADEMARK OFFICE
CERTIFICATE OF CORRECTION

PATENT NO. : 10,766,970 B2  
APPLICATION NO. : 16/311992  
DATED : September 8, 2020  
INVENTOR(S) : Welker et al.

Page 1 of 3

It is certified that error appears in the above-identified patent and that said Letters Patent is hereby corrected as shown below:

In the Specification

Column 8, Line 14: Please correct "0.5%" to read -- ±0.5% --

Column 9, Lines 27-39: Please delete the chemical structure shown for Formula II and replace it with the following:

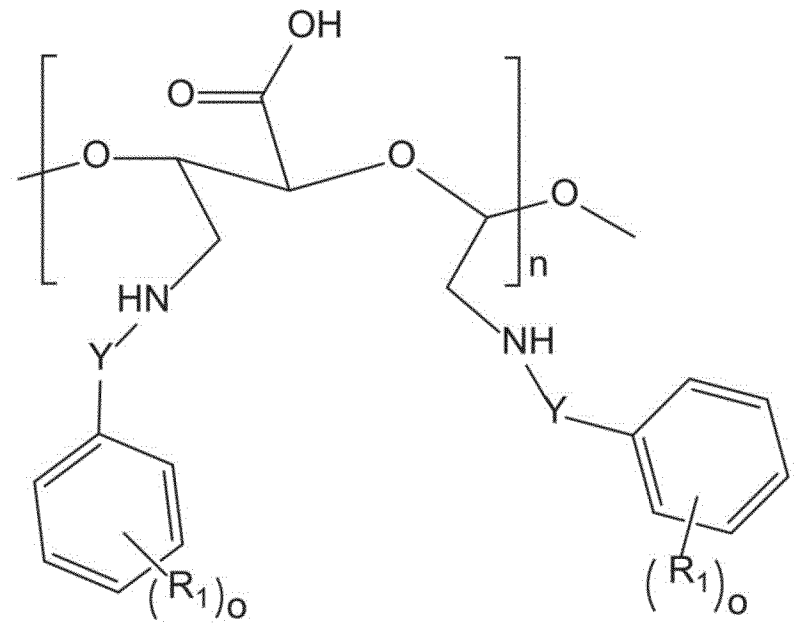

Signed and Sealed this  
Sixth Day of April, 2021

Drew Hirshfeld  
*Performing the Functions and Duties of the*  
*Under Secretary of Commerce for Intellectual Property and*  
*Director of the United States Patent and Trademark Office*

Column 16, Lines 1-43: Please delete Scheme IV and replace it with the following:
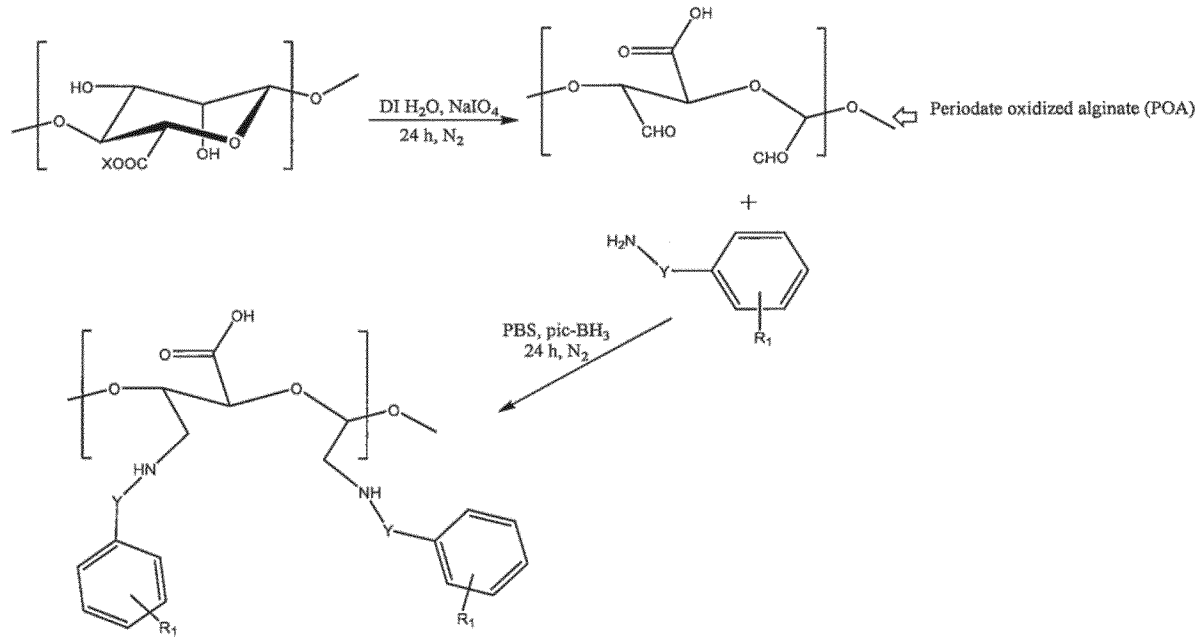
Column 16, Line 61-Column 17, Line 33: Please delete Scheme V and replace it with the following:
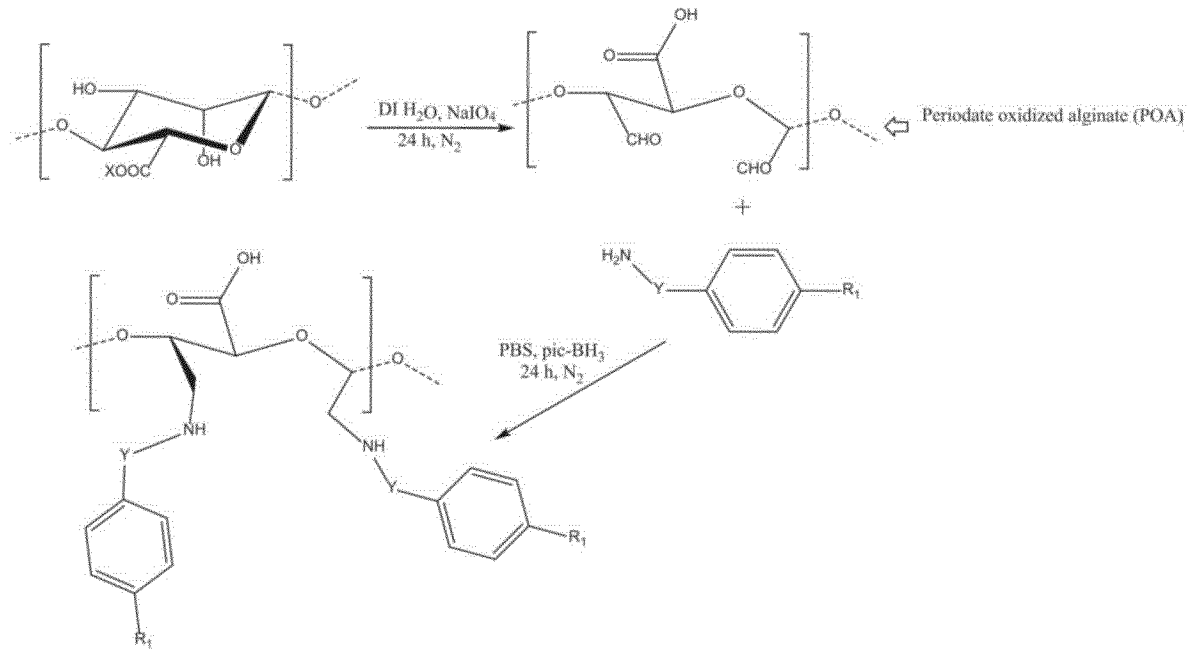

CERTIFICATE OF CORRECTION (continued)
U.S. Pat. No. 10,766,970 B2

In the Claims

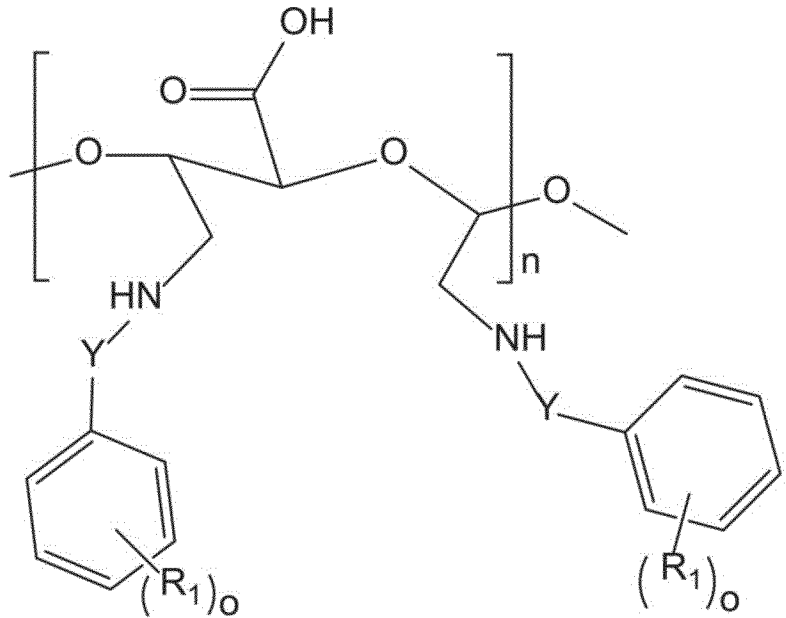

Column 39, Lines 20-33, Claim 2: Please delete the chemical structure shown for Formula II and replace it with the following: